United States Patent
Skirgaila et al.

(10) Patent No.: US 9,885,025 B2
(45) Date of Patent: Feb. 6, 2018

(54) PHI29 DNA POLYMERASE MUTANTS HAVING INCREASED THERMOSTABILITY AND PROCESSIVITY

(71) Applicant: Thermo Fisher Scientific Baltics UAB, Vilnius (LT)

(72) Inventors: Remigijus Skirgaila, Vilnius (LT); Tadas Povilaitis, Vilnius (LT)

(73) Assignee: Thermo Fisher Scientific Baltics UAB, Vilnius (LT)

( * ) Notice: Subject to any disclaimer, the term of this patent is extended or adjusted under 35 U.S.C. 154(b) by 12 days.

(21) Appl. No.: 15/209,992

(22) Filed: Jul. 14, 2016

(65) Prior Publication Data
US 2017/0015980 A1 Jan. 19, 2017

Related U.S. Application Data

(62) Division of application No. 14/135,860, filed on Dec. 20, 2013, now Pat. No. 9,422,535.

(60) Provisional application No. 61/815,893, filed on Apr. 25, 2013.

(51) Int. Cl.
*C12N 9/12* (2006.01)
*C12P 19/34* (2006.01)

(52) U.S. Cl.
CPC ............ *C12N 9/1252* (2013.01); *C12P 19/34* (2013.01); *C12Y 207/07007* (2013.01); *Y02P 20/52* (2015.11)

(58) Field of Classification Search
CPC ........... C12N 9/1252; C12Y 207/07007; C12P 19/34; Y02P 20/52
See application file for complete search history.

(56) References Cited

U.S. PATENT DOCUMENTS

| | | |
|---|---|---|
| 5,196,543 A | 3/1993 | Blanco et al. |
| 8,420,366 B2 | 4/2013 | Clark et al. |
| 8,906,660 B2 | 12/2014 | Kamtekar et al. |
| 2010/0093555 A1 | 4/2010 | Bjornson et al. |
| 2010/0112645 A1 | 5/2010 | Clark et al. |
| 2011/0165652 A1 | 7/2011 | Hardin et al. |
| 2011/0195457 A1 | 8/2011 | Nelson et al. |
| 2012/0034602 A1 | 2/2012 | Emig et al. |

(Continued)

FOREIGN PATENT DOCUMENTS

| | | |
|---|---|---|
| EP | 2089517 | 10/2006 |
| EP | 1963536 | 9/2008 |

(Continued)

OTHER PUBLICATIONS

Telenius et al. Degenerate Oligonucleotide-Primed PCR: General Amplification of Target DNA by a Single Degenerate Primer. Genomics 13 (1992) 718-725.

(Continued)

*Primary Examiner* — Alexander D Kim
(74) *Attorney, Agent, or Firm* — McNeill Bauer PLLC

(57) ABSTRACT

Mutants of bacteriophage phi29 DNA polymerase with increased protein stability and increased half-life, compared to wild type DNA polymerase. The disclosed mutants are more stable in reaction mixtures with or without DNA. The inventive phi29 DNA polymerase mutants generate more amplification product. The inventive phi29 DNA polymerase mutants amplify genomic DNA with less bias compared to wild type DNA polymerase. Selected mutations increase the affinity of polymerase for DNA template.

17 Claims, 16 Drawing Sheets

DNA binding assay of phi29 polymerase mutants

(56) References Cited

U.S. PATENT DOCUMENTS

2013/0217007 A1  8/2013  Kamtekar et al.
2014/0094374 A1  4/2014  Kamtekar et al.

FOREIGN PATENT DOCUMENTS

WO  WO 2007/076057  7/2007
WO  WO 2008/051530  5/2008
WO  WO 2009/091847  7/2009

OTHER PUBLICATIONS

Zhang et al. Whole genome amplification from a single cell: Implications for genetic analysis. Proc Natl Acad Sci U S A. 89 (1992) 5847-5851.
Rosenthal et al. Geonomic walking and sequencing by oligo-cassette mediated polymerase chain reaction. Nucleic Acids Res. 18 (1990) 3095-3096.
Dean et al. Comprehensive human genome amplification using multiple displacement amplification 99 (2002) 5261-5266.
Henry et al. The evolution of DNA polymerases with novel activities. Curr Opin Biotechnol. 16 (2005) 370-377.
Marine et al. Caught in the middle with multiple displacement amplification: the myth of pooling for avoiding multiple displacement amplification bias in a metagenome. Microbiome (2014) 1-8.
Alsmadi et al. Specific and complete human genome amplification with improved yield achieved by phi29 DNA polymerase and a novel primer at elevated temperature BMC Res Notes 2 (2009) 1-7.
Ghadessy et al. Generic expansion of the substrate spectrum of a DNA polymerase by directed evolution. Nat Biotechnol 22 (2004) 755-759.
d'Abbadie et al. Molecular breeding of polymerases for amplification of ancient DNA. Nat Biotechnol 25 (2007) 939-943.
Ong et al. Directed Evolution of DNA Polymerase, RNA Polymerase and Reverse Transcriptase Activity in a Single Polypeptide. J Mol Biol 361 (2006) 537-550.
Loakes, et al. Evolving a Polymerase for Hydrophobic Base Analogues. J Am Chem Soc 131 (2009) 14827-14837.
Ramsay et al. CyDNA: Synthesis and Replication of Highly Cy-Dye Substituted DNA by an Evolved Polymerase. J Am Chem Soc. 132 (2010) 5096-5104.
Tubeleviciute et al. Compartmentalized self-replication (CSR) selection of Thermococcus litoralis Sh1B DNA polymerase for diminished uracil binding Protein Eng Des Sel 23 (2010) 589-597.
Baar et al. Molecular breeding of polymerases for resistance to environmental inhibitors Nucleic Acids Res 39 (2011) 1-12.
Zaccolo et al. An Approach to Random Mutagenesis of DNA Using Mixtures of Triphosphate Derivatives of Nucleoside Analogues. J Mol Biol 255 (1996) 589-603.
Williams et al. Amplification of complex gene libraries by emulsion PCR. Nat Methods 3 (2006) 545-550.
Bark, S. Site-Directed Mutagenesis by Double Polymerase Chain Reaction. Mol Biotechnol 3 (1995) 1-7.
Mokry et al. Accurate SNP and mutation detection by targeted custom microarray-based genomic enrichment of short-fragment sequencing libraries. Nucleic Acids Res 38 (2010) 1-9.
Silander et al. Whole Genome Amplification with Phi29 DNA Polymerase to Enable Genetic or Genomic Analysis of Samples of Low DNA Yield. Methods Mol Biol 439 (2008) 1-18.
Blanco et al. Mutational Analysis of Bacteriophage ø29 DNA Polymerase. Methods Enzymol 262 (1995) 283-294.
Sakaguchi, et al. Role of Proline Residues in Conferring Thermostability on Aqualysin. J Biochem 141 (2007) 213-220.
del Prado et al. Dual Role of ø29 DNA Polymerase Lys529 in Stabilisation of the DNA Priming-Terminus and the Terminal Protein Priming Residue at the Polymerisation Site. PLoS One 8 (2013) 1-11.

de Vega et al. Mutational Analysis of ø29 DNA Polymerase Residues Acting as ssDNA Ligants for 3'-5' Exonucleolysis. J Mol Biol 279 (1998) 807-822.
Sasaki et al. Effect of molecular crowding on DNA polymerase activity. *Biotechnology Journal* 2006, 1, 440-446.
Eom et al. Structure of Taq polymerase with DNA at the polymerase active site. *Nature* vol. 382 Jul. 18, 1996, pp. 278-281.
Alsmadi et al. Specific and complete human genome amplification with improved yield achieved by phi29 DNA polymerase and a novel primer at elevated temperature. BMC Research Notes 2 (2009), 7 pages.
Bernad et al. Structural and functional relationships between prokaryotic and eukaryotic DNA polymerases. The EMBO Journal 6 (1987) 4219-4225.
Berman et al. Structures of the phi29 DNA polymerase complexed with substrate: the mechanism of translocation in B-family polymerases. The EMBO Journal 26 (2007) 3494-3505.
Blanco et al. Highly Efficient DNA Synthesis by the Phage φ29 DNA Polymerase: Symmetrical Mode of DNA Replication. J. Biol. Chem 264 (1989) 8935-8940.
Dufour et al. An Aspartic Acid residue in TPR-1, a Specific Region of Protein-priming DNA Polymerases, is Required for the Functional Interaction with Primer Terminal Protein. J. Mol. Biol. 34 (2000), 289-300.
Esteban et al. Fidelity of the φ29 DNA Polymerase: Comparison between Protein-Primed Initiation and DNA Polymerization. J. Biol. Chem 268 (1993) 2719-2726.
Esteban et al. 3'→5' Exonuclease Active Site of φ29 DNA Polymerase: Evidence Favoring a Metal Ion-Assisted Reaction Mechanism. J. Biol. Chem. 269 (1994) 31946-31954.
Hutchison et al. Cell-free cloning using φ29 DNA polymerase. Proc. Nat. Acad. Sci. 102 (2005) 17332-17336.
Johne et al. Rolling-circle amplification of viral DNA genomes using phi29 polymerase. Trends in Microbiology 17 (2009) 205-211.
Kamtekar et al. Insights into Strand Displacement and Processivity from the Crystal Structure of the Protein-Primed DNA Polymerase of Bacteriophage φ29. Molecular Cell 16 (2004) 609-618.
Lizardi et al. Mutation detection and single-molecule counting using isothermal rolling-circle amplification. Nature Genetics 19 (1998) 225-232.
Rodriguez et al. A specific subdomain in φ29 DNA polymerase confers both processivity and strand-displacement capacity. Proc. Nat. Acad. Sci. 102 (2005) 6407-6412.
Sales and de Vega. Bacteriophage protein-primed DNA replication. Recent Advances in DNA Virus Replication (2006), pp. 259-288.
Lieberman et al. Processive Replication of single DNA molecules in a nanopore catalyzed by phi29 DNA polymerase. J. Am. Chem. Soc. 132 (2010) 17961-17972.
De Vega et al. Improvement of phi29 DNA polymerase amplification by fusion of DNA binding motifs. Proc. Natl. Acad. Sci. U.S.A. 107 (2010) 16506-16511.
Ghadessy et al. Directed evolution of polymerase function by compartmentalized self-replication. Proc. Natl. Acad. Sci. USA 98 (2001) 4552-4557.
Merkiene et al. Direct detection of RNA in vitro and in situ by target-primed RCA: The impact of *E. coli* RNase III on the detection efficiency of RNA sequences distanced far from the 3'-end. RNA. 16 (2010) 1508-1515.
Hosono et al. Unbiased whole-genome amplification directly from clinical samples. Genome Research. 13 (2003) 954-964.
Mokry et al. Accurate SNP and mutation detection by targeted custom microarray-based genomic enrichment of short-fragment sequencing libraries. Nucleic Acids Res. 38 (2010) e116.
Beyer et al. Periodic DNA Nanotemplates Synthesized by Rolling Circle Amplification. Nano Letters. 4 (2005) 719-722.
Pan et al. A procedure for highly specific, sensitive, and unbiased whole-genome amplification. PNAS. 105 (2008) 15499-15504.
International Search Report PCT/EP2010/063223, dated Mar. 3, 2011, 3 pages.
Partial European Search Report for EP 14165903.7, dated Oct. 28, 2014, 9 pages.

(56) References Cited

OTHER PUBLICATIONS

Extended European Search Report for EP 14165903.7, dated Feb. 16, 2016, 10 pages.
File History of U.S. Appl. No. 14/135,860, filed Dec. 20, 2013, available on PAIR.
Extended European Search Report received in EP 16163265.8, dated Oct. 4, 2016, 6 pages.

FIG. 1. Substitutions of amino acids residues found in selected clones

| Group | Mutations | Substitutions |
|---|---|---|
| Group4 M3 | 13 mutations | 8M->R, 15T->A, 49A->T, 51V->A, 53K->Q, 97M->T, 197G->D, 221E->K, 312G->S, 497Q->P, 512K->E, 526F->L, 530C->F |
| Group10 M11 | 13 mutations | 8M->R, 51V->A, 70I->T, 97M->T, 197G->D, 214L->S, 221E->K, 337K->E, 434T->A, 514V->I, 515E->A, 534T->P, 575K->R |
| Group12 M14 | 13 mutations | 51V->A, 97M->T, 197G->D, 221E->K, 247V->A, 260S->N, 453I->V, 514V->I, 515E->A, 534T->P, 536K->R, 555K->R, 575K->R |
| Group14 M16 | 11 mutations | 8M->R, 15T->A, 51V->A, 53K->Q, 97M->T, 197G->D, 221E->K, 359L->S, 497Q->P, 512K->E, 526F->L |
| Group18 M24 | 11 mutations | 8M->R, 107L->S, 123L->S, 172I->V, 239E->G, 272E->K, 434T->A, 478K->E, 497Q->P, 526F->L, 553K->R |
| Group13 M15 | 10 mutations | 8M->R, 15T->A, 51V->A, 53K->Q, 97M->T, 197G->D, 221E->K, 497Q->P, 512K->E, 526F->L |
| Group16 M20 | 10 mutations | 8M->R, 51V->A, 97M->T, 197G->D, 221E->K, 237F->S, 291E->G, 497Q->P, 512K->E, 526F->L |
| Group5 M4 | 9 mutations | 8M->R, 107L->S, 123L->S, 239E->G, 434T->A, 478K->E, 497Q->P, 526F->L, 553K->R |
| Group7 M7 | 9 mutations | 51V->A, 57D->N, 97M->T, 197G->D, 221E->K, 280D->G, 497Q->P, 512K->E, 526F->L |
| Group8 M9 | 9 mutations | 8M->R, 51V->A, 97M->T, 197G->D, 221E->K, 246M->T, 497Q->P, 512K->E, 526F->L |
| Group9 M10 | 9 mutations | 8M->R, 51V->A, 97M->T, 197G->D, 221E->K, 378I->V, 497Q->P, 512K->E, 526F->L |
| Group11 M13 | 9 mutations | 8M->R, 97M->T, 197G->D, 221E->K, 337K->E, 514V->I, 515E->A, 534T->P, 575K->R |
| Group17 M23 | 9 mutations | 51V->A, 97M->T, 110K->E, 197G->D, 221E->K, 410G->E, 497Q->P, 512K->E, 526F->L |
| Group19 M25 | 9 mutations | 8M->R, 117T->A, 123L->S, 239E->G, 437A->G, 490K->R, 514V->I, 515E->A, 534T->P |
| Group21 M27 | 9 mutations | 8M->R, 91N->S, 123L->S, 188M->V, 239E->G, 354K->E, 497Q->P, 512K->E, 526F->L |
| Group2 M1, M6, M8, M12 | 8 mutations | 51V->A, 97M->T, 197G->D, 209K->E, 221E->K, 497Q->P, 512K->E, 526F->L |
| Group15 M18 | 8 mutations | 51V->A, 97M->T, 186D->G, 197G->D, 221E->K, 497Q->P, 512K->E, 526F->L |
| Group20 M26 | 8 mutations | 51V->A, 97M->T, 197G->D, 221E->K, 276V->A, 497Q->P, 512K->E, 526F->L |
| Group3 M2, M17, M19, M21-22, M28-30 | 7 mutations | 51V->A, 97M->T, 197G->D, 221E->K, 497Q->P, 512K->E, 526F->L |
| Group6 M5 | 7 mutations | 51V->A, 97M->T, 197G->D, 221E->K, 478K->E, 515E->A, 526F->L |
| WildTypeGroup (WT) | 0 mutations | |

FIG. 2. The CLUSTALW alignment of 30 selected protein sequences

| | | | | | | | | | |
|---|---|---|---|---|---|---|---|---|---|
| wt  | 1 | MKHMPRKMYS | CDFETTTKVE | DCRVWAYGYM | NIEDHSEYKI | GNSLDEFMAW | VLKVQADLYF | HNLKFDGAFI | INWLERNGFK | WSADGLPNTY | NTIISRMGQW |
| M1  | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M2  | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M3  | 1 | MKHMPRKRYS | CDFETTKVE  | DCRVWAYGYM | NIEDHSEYKI | GNSLDEFMAW | ALQVQADLYF | HNLKFDGAFI | INWLERNGFK | WSADGLPNTY | NTIISRTGQW |
| M4  | 1 | MKHMPRKRYS | CDFETTKVE  | DCRVWAYGYM | NIEDHSEYKI | GNSLDEFMAW | VLKVQADLYF | HNLKFDGAFI | INWLERNGFK | WSADGLPNTY | NTIISRMGQW |
| M5  | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M6  | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M7  | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M8  | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M9  | 1 | MKHMPRKRYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M10 | 1 | MKHMPRKRYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M11 | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M12 | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M13 | 1 | MKHMPRKMYS | CDFETTTKVE | DCRVWAYGYM | NIEDHSEYKI | GNSLDEFMAW | VLKVQADLYF | HNLKFDGAFI | INWLERNGFK | WSADGLPNTY | NTIISRTGQW |
| M14 | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M15 | 1 | MKHMPRKRYS | CDFETTTKVE | DCRVWAYGYM | NIEDHSEYKI | GNSLDEFMAW | ALQVQADLYF | HNLKFDGAFI | INWLERNGFK | WSADGLPNTY | NTIISRTGQW |
| M16 | 1 | MKHMPRKRYS | CDFEATTKVE | DCRVWAYGYM | NIEDHSEYKI | GNSLDEFMAW | ALQVQADLYF | HNLKFDGAFI | INWLERNGFK | WSADGLPNTY | NTIISRTGQW |
| M17 | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M18 | 1 | MKHMPRKRYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M19 | 1 | MKHMPRKRYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M20 | 1 | MKHMPRKRYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M21 | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M22 | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M23 | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M24 | 1 | MKHMPRKMYS | CDFETTTKVE | DCRVWAYGYM | NIEDHSEYKI | GNSLDEFMAW | VLKVQADLYF | HNLKFDGAFI | INWLERNGFK | WSADGLPNTY | NTIISRMGQW |
| M25 | 1 | MKHMPRKRYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M26 | 1 | MKHMPRKRYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M27 | 1 | MKHMPRKMYS | CDFETTTKVE | DCRVWAYGYM | NIEDHSEYKI | GNSLDEFMAW | VLKVQADLYF | HNLKFDGAFI | INWLERNGFK | WSADGLPNTY | NTIISRMGQW |
| M28 | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | STIISRMGQW |
| M29 | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |
| M30 | 1 | MKHMPRKMYS | CDFETTTKVE | DCRVWAYGYM | NIEDHSEYKI | GNSLDEFMAW | ALKVQADLYF | HNLKFDGAFI | INWLERNGFK | WSADGLPNTY | NTIISRTGQW |

FIG. 2. continued

| | | | | | | | | | | |
|---|---|---|---|---|---|---|---|---|---|---|
| wt | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKGFKD |
| M1 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M2 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M3 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M4 | 101 | YMIDICLGYK | GKRKIHTVIY | DSSKKLPFPV | KKIAKDFKLT | VLKGDIDYHK | ERPVGYKITP | EEYAYIKNDI | QIIAEALLIQ | FKQGLDRMTA | GSDSLKDFKD |
| M5 | 101 | YMIDICSGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKGFKD |
| M6 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M7 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M8 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M9 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M10 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M11 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M12 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M13 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M14 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M15 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M16 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M17 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M18 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M19 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M20 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M21 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M22 | 101 | YMIDICLGYV | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M23 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M24 | 101 | YMIDICSGYK | GKRKIHTVIY | DSSKKLPFPV | KKIAKDFKLT | VLKGDIDYHK | ERPVGYKITP | EEYAYIKNDI | QVIAEALLIQ | FKQGLDRMTA | GSDSLKDFKD |
| M25 | 101 | YMIDICLGYK | GKRKIHTAIY | DSSKKLPFPV | KKIAKDFKLT | VLKGDIDYHK | ERPVGYKITP | EEYAYIKNDI | QIIAEALLIQ | FKQGLDRMTA | GSDSLKDFKD |
| M26 | 101 | YMIDICLGYK | GKRKIHTVIY | DSSKKLPFPV | KKIAKDFKLT | VLKGDIDYHK | ERPVGYKITP | EEYAYIKNDI | QIIAEALLIQ | FKQGLDRMTA | GSDSLKDFKD |
| M27 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRVTA | GSDSLKGFKD |
| M28 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M29 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |
| M30 | 101 | YMIDICLGYK | GKRKIHTVIY | DSLKKLPFPV | KKIAKDFKLT | VLKGDIDYHK | ERPVGYKITP | EEYAYIKNDI | QIIAEALLIQ | FKQGLDRMTA | GSDSLKDFKD |

FIG. 2. continued

| | | | | | | | | | | |
|---|---|---|---|---|---|---|---|---|---|---|
| wt  | 201 | IITTKKFKKV | FPTLSLGLDK | EVRYAYRGGF | TWLNDRFKEK | EIGEGMVFDV | NSLYPAQMYS | RLLPYGEPIV | FEGKYVWDED | YPLHIQHIRC | EFELKEGYIP |
| M1  | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M2  | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M3  | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M4  | 201 | IITTKKFKKV | FPTLSLGLDK | EVRYAYRGGF | TWLNDRFKEK | EIGEGMVFDV | NSLYPAQMYS | RLLPYGEPIV | FEGKYVWDED | YPLHIQHIRC | EFELKEGYIP |
| M5  | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M6  | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M7  | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M8  | 201 | IITTKKFKKV | FPTLSLGLDK | KVRYAYRGGF | TWLNDRFKEK | EIGEGVFDV  | NSLYPAQMYS | RLLPYGEPIV | FEGKYVWDED | YPLHIQHIRC | EFELKEGYIP |
| M9  | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M10 | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M11 | 201 | IITTKKFKKV | FPTSSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M12 | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M13 | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M14 | 201 | IITTKKFKKV | FPTLSLGLDK | KVRYAYRGGF | TWLNDRFKEK | EIGEGMVFDV | NSLYPAQMYN | RLLPYGEPIV | FEGKYVWDED | YPLHIQHIRC | EFELKEGYIP |
| M15 | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M16 | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M17 | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M18 | 201 | IITTKKFKKV | FPTLSLGLDK | KVRYAYRGGF | TWLNDRFKCK | EIGEGMVFDV | NSLYPAQMYS | RLLPYGEPIV | FEGKYVWDED | YPLHIQHIRC | EFELKEGYIP |
| M19 | 201 | IITTKKFKKV | FPTLSLGLDK | KVRYAYRGGF | TWLNDRFKCK | EIGEGMVFDV | NSLYPAQMYS | RLLPYGEPIV | FEGKYVWDED | YPLHIQHIRC | EFELKEGYIP |
| M20 | 201 | IITTKKFKKV | FPTLSLGLDK | KVRYAYRGGF | TWLNDRSKEK | EIGEGMVFDV | NSLYPAQMYS | RLLPYGEPIV | FEGKYVWDED | YPLHIQHIRC | EFELKEGYIP |
| M21 | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M22 | 201 | IITTKKFKKV | FPTLSLGLDK | KVRYAYRGGF | TWLNDRFKEK | EIGEGMVFDV | NSLYPAQMYS | RLLPYGEPIV | FEGKYVWDED | YPLHIQHIRC | EFELKEGYIP |
| M23 | 201 | IITTKKFKKV | FPTLSLGLDK | KVRYAYRGGF | TWLNDRFKCK | EIGEGMVFDV | NSLYPAQMYS | RLLPYGEPIV | FEGKYVWDED | YPLHIQHIRC | EFELKEGYIP |
| M24 | 201 | IITTKKFKKV | FPTLSLGLDK | EVRYAYRGGF | TWLNDRFKEK | EIGEGMVFDV | NSLYPAQMYS | RLLPYGEPIV | FEGKYVWDED | YPLHIQHIRC | EFELKEGYIP |
| M25 | 201 | IITTKKFKKV | FPTLSLGLDK | EVRYAYRGGF | TWLNDRFKEK | EIGEGMVFDV | NSLYPAQMYS | RLLPYGEPIV | FEGKYVWDED | YPLHIQHIRC | EFELKEGYIP |
| M26 | 201 | IITTKKFKKV | FPTLSLGLDK | EVRYAYRGGF | TWLNDRFKEK | EIGEGMVFDV | NSLYPAQMYS | RLLPYGEPIV | FEGKYVWDED | YPLHIQHIRC | EFELKEGYIP |
| M27 | 201 | IITTKKFKKV | FPTLSLGLDK | EVRYAYRGGF | TWLNDRFKEK | EIGEGMVFDV | NSLYPAQMYS | RLLPYGEPIV | FEGKYWDED  | YPLHIQHIRC | EFELKEGYIP |
| M28 | 201 | IITTKKFKKV | FPTLSLGLDK | EVRYAYRGGF | TWLNDRFKEK | EIGEGMVFDV | NSLYPAQMYS | RLLPYGEPIV | FEGKYVWDED | YPLHIQHIRC | EFELKEGYIP |
| M29 | 201 | IITTKKFKKV | FPTLSLGLDK | EVRYAYRGGF | TWLNDRFKEK | EIGEGMVFDV | NSLYPAQMYS | RLLPYGEPIV | FEGKYVWDED | YPLHIQHIRC | EFELKEGYIP |
| M30 | 201 | IITTKKFKKV | FPTLSLGLDK | EVRYAYRGGF | TWLNDRFKEK | EIGEGMVFDV | NSLYPAQMYS | RLLPYGEPIV | FEGKYVWDED | YPLHIQHIRC | EFELKEGYIP |

FIG. 2. continued

| | | | | | | | | | | |
|---|---|---|---|---|---|---|---|---|---|---|
| wt | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M1 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M2 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKTASN DVT |
| M3 | 301 | TIQIKRSRFY | KSNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M4 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M5 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M6 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M7 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M8 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M9 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M10 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M11 | 301 | TIQIKRSRFY | KGNEYLKSSG | GEIADLWLSN | VDLELMKEHY | DLYNVEYISG | LKFKATTGLF | KDFIDKWTYI | KTTSEGAVKQ | LAKLMLNSLY | GKFASNPDVT |
| M12 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M13 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M14 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M15 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M16 | 301 | TIQIKRSRFY | KGNEYLKSSG | GEIADLWLSN | VDLELMKEHY | DLYNVEYISG | LKFKATTGSF | KDFIDKWTYI | KTTSEGAIKQ | LAKLMLNSLY | GKFASNPDVT |
| M17 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M18 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M19 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M20 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M21 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M22 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M23 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M24 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M25 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M26 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M27 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M28 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M29 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |
| M30 | 301 | TIQIKRSRFY | KGNEYLKSSG | GEIADLWLSN | VDLELMKEHY | DLYNVEYISG | LKFKATTGLF | KDFIDKWTYI | KTTSEGAIKQ | LAKLMLNSLY | GKFASNPDVT |

| | | | | | | | | | |
|---|---|---|---|---|---|---|---|---|---|
| wt | 501 | IQDIYMKEVD | GKLVEGSPDD | YTDIKFSVKC | AGMTDKIKKE | VTFENFKVGF | SRKMKPKPVQ | VPGGVVLVDD | TFTIK |
| M1 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M2 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M3 | 501 | IQDIYMKEVD | GELVEGSPDD | YTDIKTSVKF | AGMTDKIKKE | VTFENFKVGF | SRKMKPKPVQ | VPGGVVLVDD | TFTIK |
| M4 | 501 | IQDIYMKEVD | GKLVEGSPDD | YTDIKTSVKC | AGMTDKIKKE | VTFENFKVGF | SRKMKPKPVQ | VPGGVVLVDD | TFTIK |
| M5 | 501 | IQDIYMKEVD | GKLVTAGSPDD | YTDIKFSVKC | AGMTDKIKKE | VTFENFKVGF | SRRMKPKPVQ | VPGGVVLVDD | TFTIK |
| M6 | 501 | IQDIYMKEVD | GELVEGSPDD | YTDIKTSVKC | AGMTDKIKKE | VTFENFKVGF | SRKMKPKPVQ | VPGGVVLVDD | TFTIKQT |
| M7 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M8 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M9 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M10 | 501 | IQDIYMKEVD | GKLVEGSPDD | YTDIKFSVKC | AGMPDKIKKE | VTFENFKVGF | SRKMRPKPVQ | VPGGVVLVDD | TFTIK |
| M11 | 501 | IQDIYMKEVD | GKLTAGSPDD | YTDIKTSVKC | AGMTDKIKKE | VTFENFKVGF | SRKMKPKPVQ | VPGGVVLVDD | TFTIR |
| M12 | 501 | IQDIYMKEVD | GKLTAGSPDD | YTDIKTSVKC | AGMPDKIKKE | VTFENFKVGF | SRKMKPKPVQ | VPGGVVLVDD | TFTIR |
| M13 | 501 | IQDIYMKEVD | GKLTAGSPDD | YTDIKFSVKC | AGMPDRIKKE | VTFENFKVGF | SRKMKPKPVQ | VPGGVVLVDD | TFTIR |
| M14 | 501 | IQDIYMKEVD | GKLVEGSPDD | YTDIKFSVKC | AGMPDKIKKE | VTFENFKVGF | SRKMKPKPVQ | VPGGVVLVDD | TFTIK |
| M15 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M16 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M17 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M18 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M19 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M20 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M21 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M22 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M23 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M24 | 501 | IQDIYMKEVD | GELVEGSPDD | YTDIKTSVKC | AGMTDKIKKE | VTFENFKVGF | SRRMKPKPVQ | VPGGVVLVDD | TFTIK |
| M25 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M26 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M27 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M28 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M29 | 501 | IQDIYMKEVD | GELVEGSPDD | YTDIKTSVKC | AGMTDKIKKE | VTFENFKVGF | SRKMKPKPVQ | VPGGVVLVDD | TFTIK |
| M30 | 501 | IQDIYMKEVD | GELVEGSPDD | YTDIKTSVKC | AGMTDKIKKE | VTFENFKVGF | SRKMKPKPVQ | VPGGVVLVDD | TFTIK |

FIGS. 3A-F. Comparison of half-life ($T_{1/2}$) activities between wild-type and mutant variants of phi29 DNA polymerase FIGS. 4A-B. Comparison of half-life ($T_{1/2}$) activities between wild-type and mutant variants containing single mutations G197D, E221K FIGS. 5A-C. Comparison of MDA efficiency between wild-type and mutant variants of phi29 DNA polymerase

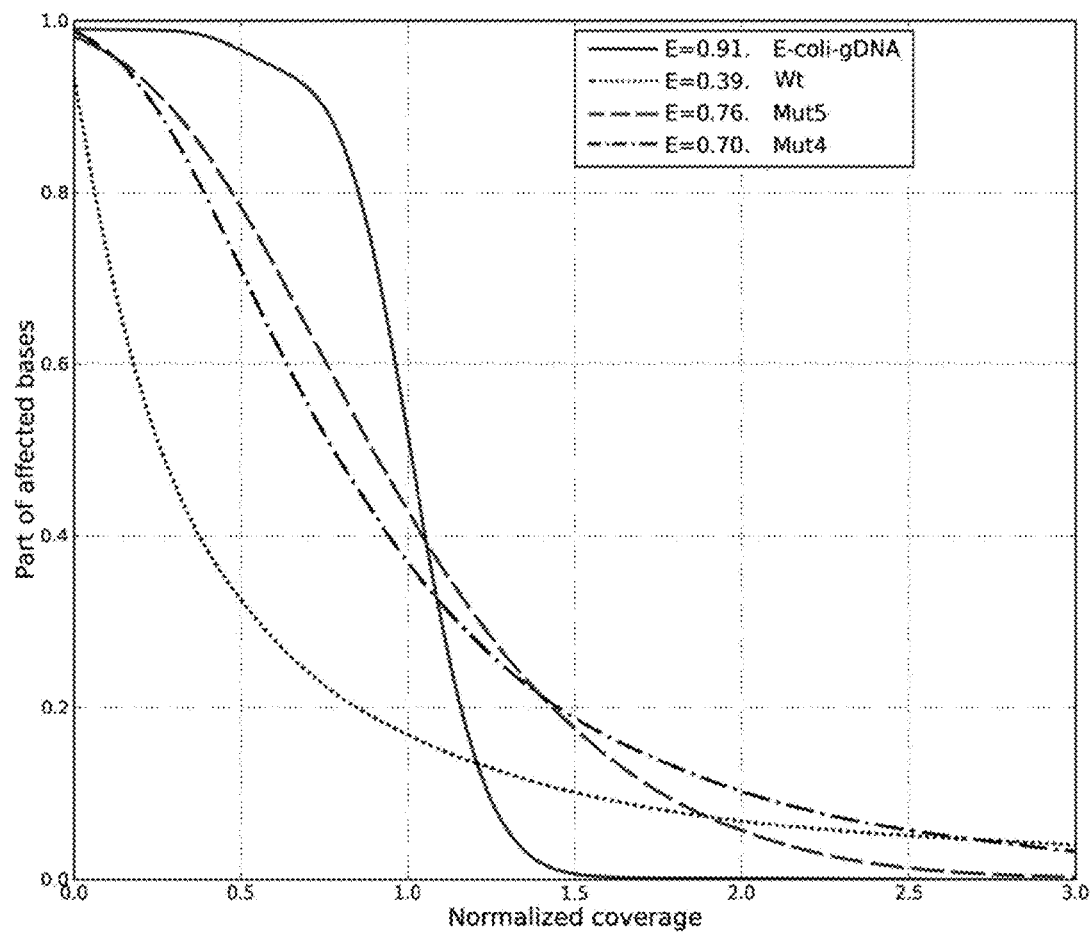
FIG. 6. Coverage evenness

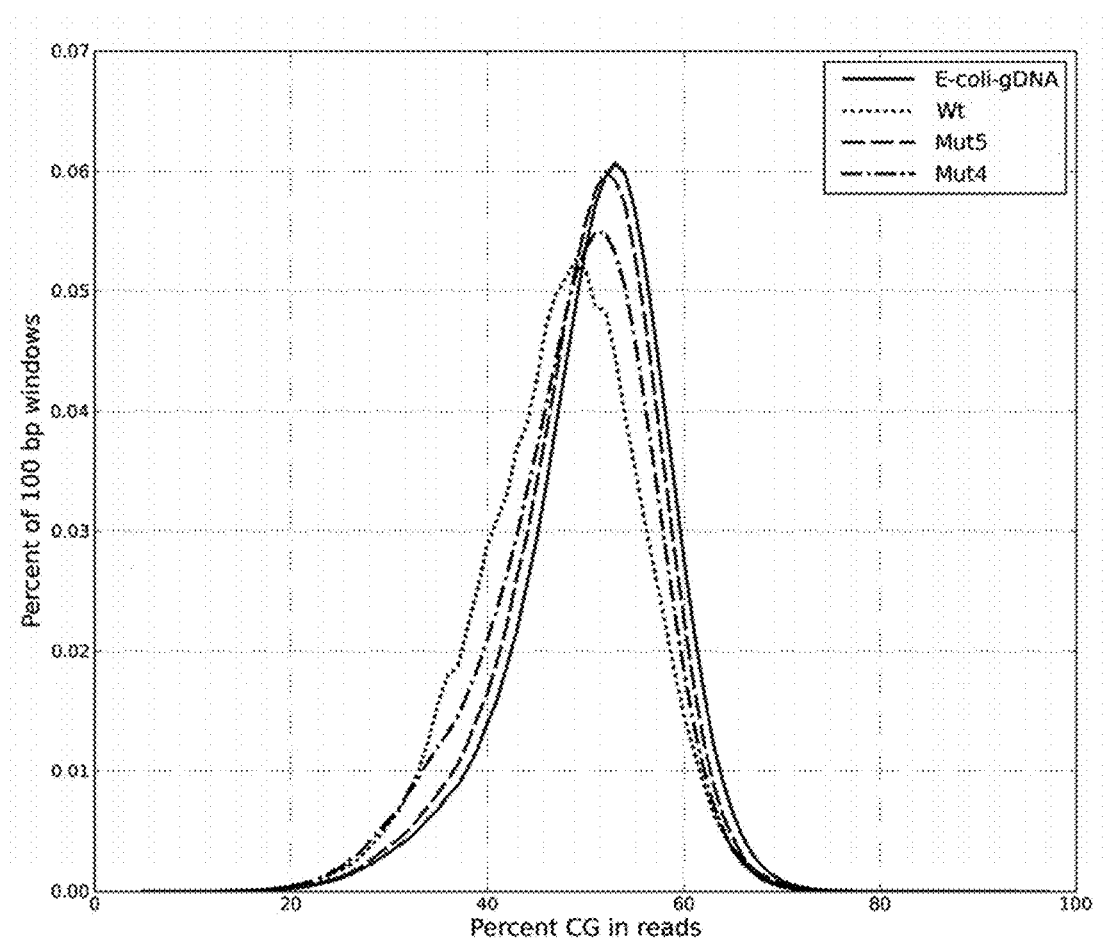
FIG. 7. CG content of read sequences.

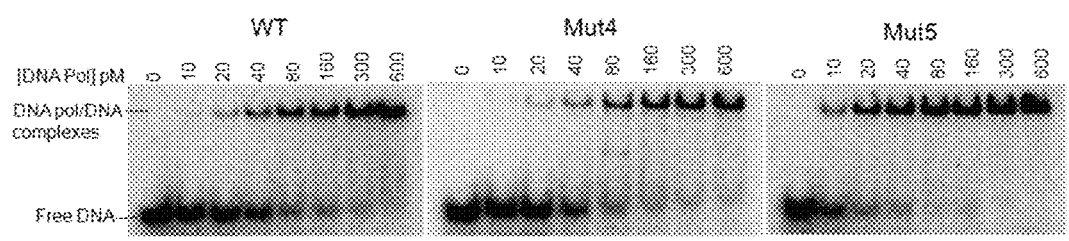
FIG. 8. DNA binding assay of phi29 polymerase mutants

SEQUENCE LISTING

<160> NUMBER OF SEQ ID NOS: 40

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: misc_feature
<222> LOCATION: (24)..(26)
<223> OTHER INFORMATION: Phosphorothioate between positions

<400> SEQUENCE: 1

-continued cagctgcatt aatgaatcgg ccaacg                                                26

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (18)..(20)
<223> OTHER INFORMATION: Phosphorothioate between positions

<400> SEQUENCE: 2
ttagcagccg gatctcagtg                                                       20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcgagcccga tcttccccat cg                                                    22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttagcagccg gatctcagtg                                                       20

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gttgggaagg gcgatcg                                                          17

<210> SEQ ID NO 7
<211> LENGTH: 21
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 7
actttatgct tccggctcgt a                                              21

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatcacagtg agtac                                                    15

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tctattgtac tcactgtgat c                                              21

<210> SEQ ID NO 10
<211> LENGTH: 575
<212> TYPE: PRT
<213> ORGANISM: Bacillus phage phi29

<400> SEQUENCE: 10
```

Met Lys His Met Pro Arg Lys Met Tyr Ser Cys Asp Phe Glu Thr Thr
 1               5                  10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

```
Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 11
<211> LENGTH: 575
<212> TYPE: PRT
<213> ORGANISM: Bacillus phage phi29

<400> SEQUENCE: 11

Met Lys His Met Pro Arg Lys Met Tyr Ser Cys Asp Phe Glu Thr Thr
```

-continued

```
1               5                   10                  15

Thr Lys Val Glu Asp Cys Arg Val Trp Ala Tyr Gly Tyr Met Asn Ile
                20                  25                  30
Glu Asp His Ser Glu Tyr Lys Ile Gly Asn Ser Leu Asp Glu Phe Met
                35                  40                  45
Ala Trp Ala Leu Lys Val Gln Ala Asp Leu Tyr Phe His Asn Leu Lys
 50                  55                  60
Phe Asp Gly Ala Phe Ile Ile Asn Trp Leu Glu Arg Asn Gly Phe Lys
 65                  70                  75                  80
Trp Ser Ala Asp Gly Leu Pro Asn Thr Tyr Asn Thr Ile Ile Ser Arg
                85                  90                  95
Thr Gly Gln Trp Tyr Met Ile Asp Ile Cys Leu Gly Tyr Lys Gly Lys
                100                 105                 110
Arg Lys Ile His Thr Val Ile Tyr Asp Ser Leu Lys Lys Leu Pro Phe
                115                 120                 125
Pro Val Lys Lys Ile Ala Lys Asp Phe Lys Leu Thr Val Leu Lys Gly
 130                 135                 140
Asp Ile Asp Tyr His Lys Glu Arg Pro Val Gly Tyr Lys Ile Thr Pro
 145                 150                 155                 160
Glu Glu Tyr Ala Tyr Ile Lys Asn Asp Ile Gln Ile Ala Glu Ala
                165                 170                 175
Leu Leu Ile Gln Phe Lys Gln Gly Leu Asp Arg Met Thr Ala Gly Ser
                180                 185                 190
Asp Ser Leu Lys Asp Phe Lys Asp Ile Ile Thr Thr Lys Lys Phe Lys
                195                 200                 205
Glu Val Phe Pro Thr Leu Ser Leu Gly Leu Asp Lys Lys Val Arg Tyr
 210                 215                 220
Ala Tyr Arg Gly Gly Phe Thr Trp Leu Asn Asp Arg Phe Lys Glu Lys
 225                 230                 235                 240
Glu Ile Gly Glu Gly Met Val Phe Asp Val Asn Ser Leu Tyr Pro Ala
                245                 250                 255
Gln Met Tyr Ser Arg Leu Leu Pro Tyr Gly Glu Pro Ile Val Phe Glu
                260                 265                 270
Gly Lys Tyr Val Trp Asp Glu Asp Tyr Pro Leu His Ile Gln His Ile
                275                 280                 285
Arg Cys Glu Phe Glu Leu Lys Glu Gly Tyr Ile Pro Thr Ile Gln Ile
                290                 295                 300
Lys Arg Ser Arg Phe Tyr Lys Gly Asn Glu Tyr Leu Lys Ser Ser Gly
 305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
                355                 360                 365
Tyr Ile Lys Thr Thr Ser Glu Gly Ala Ile Lys Gln Leu Ala Lys Leu
                370                 375                 380
Met Leu Asn Ser Leu Tyr Gly Lys Phe Ala Ser Asn Pro Asp Val Thr
 385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
                420                 425                 430
```

```
Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
                500                 505                 510

Leu Val Glu Gly Ser Pro Asp Asp Tyr Thr Asp Ile Lys Leu Ser Val
                515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 12
<211> LENGTH: 575
<212> TYPE: PRT
<213> ORGANISM: Bacillus phage phi29

<400> SEQUENCE: 12

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Lys Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
```

```
                225                 230                 235                 240
        Glu Ile Gly Glu Gly Met Val Phe Asp Val Asn Ser Leu Tyr Pro Ala
                        245                 250                 255
        Gln Met Tyr Ser Arg Leu Leu Pro Tyr Gly Glu Pro Ile Val Phe Glu
                        260                 265                 270
        Gly Lys Tyr Val Trp Asp Glu Asp Tyr Pro Leu His Ile Gln His Ile
                        275                 280                 285
        Arg Cys Glu Phe Glu Leu Lys Glu Gly Tyr Ile Pro Thr Ile Gln Ile
                    290                 295                 300
        Lys Arg Ser Arg Phe Tyr Lys Gly Asn Glu Tyr Leu Lys Ser Ser Gly
        305                 310                 315                 320
        Gly Glu Ile Ala Asp Leu Trp Leu Ser Asn Val Asp Leu Glu Leu Met
                        325                 330                 335
        Lys Glu His Tyr Asp Leu Tyr Asn Val Glu Tyr Ile Ser Gly Leu Lys
                        340                 345                 350
        Phe Lys Ala Thr Thr Gly Leu Phe Lys Asp Phe Ile Asp Lys Trp Thr
                        355                 360                 365
        Tyr Ile Lys Thr Thr Ser Glu Gly Ala Ile Lys Gln Leu Ala Lys Leu
                    370                 375                 380
        Met Leu Asn Ser Leu Tyr Gly Lys Phe Ala Ser Asn Pro Asp Val Thr
        385                 390                 395                 400
        Gly Lys Val Pro Tyr Leu Lys Glu Asn Gly Ala Leu Gly Phe Arg Leu
                        405                 410                 415
        Gly Glu Glu Glu Thr Lys Asp Pro Val Tyr Thr Pro Met Gly Val Phe
                        420                 425                 430
        Ile Thr Ala Trp Ala Arg Tyr Thr Thr Ile Thr Ala Ala Gln Ala Cys
                        435                 440                 445
        Tyr Asp Arg Ile Ile Tyr Cys Asp Thr Asp Ser Ile His Leu Thr Gly
                    450                 455                 460
        Thr Glu Ile Pro Asp Val Ile Lys Asp Ile Val Asp Pro Lys Lys Leu
        465                 470                 475                 480
        Gly Tyr Trp Ala His Glu Ser Thr Phe Lys Arg Ala Lys Tyr Leu Arg
                        485                 490                 495
        Pro Lys Thr Tyr Ile Gln Asp Ile Tyr Met Lys Glu Val Asp Gly Glu
                        500                 505                 510
        Leu Val Glu Gly Ser Pro Asp Asp Tyr Thr Asp Ile Lys Leu Ser Val
                    515                 520                 525
        Lys Cys Ala Gly Met Thr Asp Lys Ile Lys Lys Glu Val Thr Phe Glu
        530                 535                 540
        Asn Phe Lys Val Gly Phe Ser Arg Lys Met Lys Pro Lys Pro Val Gln
        545                 550                 555                 560
        Val Pro Gly Gly Val Val Leu Val Asp Asp Thr Phe Thr Ile Lys
                        565                 570                 575

<210> SEQ ID NO 13
<211> LENGTH: 575
<212> TYPE: PRT
<213> ORGANISM: Bacillus phage phi29

<400> SEQUENCE: 13

Met Lys His Met Pro Arg Lys Arg Tyr Ser Cys Asp Phe Glu Ala Thr
        1               5                   10                  15
        Thr Lys Val Glu Asp Cys Arg Val Trp Ala Tyr Gly Tyr Met Asn Ile
                    20                  25                  30
```

-continued

```
Glu Asp His Ser Glu Tyr Lys Ile Gly Asn Ser Leu Asp Glu Phe Met
             35                  40                  45
Thr Trp Ala Leu Gln Val Gln Ala Asp Leu Tyr Phe His Asn Leu Lys
 50                  55                  60
Phe Asp Gly Ala Phe Ile Ile Asn Trp Leu Glu Arg Asn Gly Phe Lys
 65                  70                  75                  80
Trp Ser Ala Asp Gly Leu Pro Asn Thr Tyr Asn Thr Ile Ile Ser Arg
                 85                  90                  95
Thr Gly Gln Trp Tyr Met Ile Asp Ile Cys Leu Gly Tyr Lys Gly Lys
                100                 105                 110
Arg Lys Ile His Thr Val Ile Tyr Asp Ser Leu Lys Lys Leu Pro Phe
            115                 120                 125
Pro Val Lys Lys Ile Ala Lys Asp Phe Lys Leu Thr Val Leu Lys Gly
    130                 135                 140
Asp Ile Asp Tyr His Lys Glu Arg Pro Val Gly Tyr Lys Ile Thr Pro
145                 150                 155                 160
Glu Glu Tyr Ala Tyr Ile Lys Asn Asp Ile Gln Ile Ala Glu Ala
                165                 170                 175
Leu Leu Ile Gln Phe Lys Gln Gly Leu Asp Arg Met Thr Ala Gly Ser
            180                 185                 190
Asp Ser Leu Lys Asp Phe Lys Asp Ile Ile Thr Thr Lys Lys Phe Lys
    195                 200                 205
Lys Val Phe Pro Thr Leu Ser Leu Gly Leu Asp Lys Lys Val Arg Tyr
    210                 215                 220
Ala Tyr Arg Gly Gly Phe Thr Trp Leu Asn Asp Arg Phe Lys Glu Lys
225                 230                 235                 240
Glu Ile Gly Glu Gly Met Val Phe Asp Val Asn Ser Leu Tyr Pro Ala
                245                 250                 255
Gln Met Tyr Ser Arg Leu Leu Pro Tyr Gly Glu Pro Ile Val Phe Glu
            260                 265                 270
Gly Lys Tyr Val Trp Asp Glu Asp Tyr Pro Leu His Ile Gln His Ile
    275                 280                 285
Arg Cys Glu Phe Glu Leu Lys Glu Gly Tyr Ile Pro Thr Ile Gln Ile
    290                 295                 300
Lys Arg Ser Arg Phe Tyr Lys Ser Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
    355                 360                 365
Tyr Ile Lys Thr Thr Ser Glu Gly Ala Ile Lys Gln Leu Ala Lys Leu
    370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
    435                 440                 445
Tyr Asp Arg Ile Ile Tyr Cys Asp Thr Asp Ser Ile His Leu Thr Gly
```

```
              450                 455                 460
Thr Glu Ile Pro Asp Val Ile Lys Asp Ile Val Asp Pro Lys Leu
465                 470                 475                 480

Gly Tyr Trp Ala His Glu Ser Thr Phe Lys Arg Ala Lys Tyr Leu Arg
                    485                 490                 495

Pro Lys Thr Tyr Ile Gln Asp Ile Tyr Met Lys Glu Val Asp Gly Glu
                500                 505                 510

Leu Val Glu Gly Ser Pro Asp Asp Tyr Thr Asp Ile Lys Leu Ser Val
                515                 520                 525

Lys Phe Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 14
<211> LENGTH: 575
<212> TYPE: PRT
<213> ORGANISM: Bacillus phage phi29

<400> SEQUENCE: 14

Met Lys His Met Pro Arg Lys Arg Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
        50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Ser Gly Tyr Lys Gly Lys
                100                 105                 110

Arg Lys Ile His Thr Val Ile Tyr Asp Ser Ser Lys Lys Leu Pro Phe
            115                 120                 125

Pro Val Lys Lys Ile Ala Lys Asp Phe Lys Leu Thr Val Leu Lys Gly
        130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
        210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Val Asn Ser Leu Tyr Pro Ala
                245                 250                 255
```

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Ala Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Glu Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Leu Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Arg Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 15
<211> LENGTH: 577
<212> TYPE: PRT
<213> ORGANISM: Bacillus phage phi29

<400> SEQUENCE: 15

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

-continued

```
Phe Asp Gly Ala Phe Ile Ile Asn Trp Leu Glu Arg Asn Gly Phe Lys
 65                  70                  75                  80

Trp Ser Ala Asp Gly Leu Pro Asn Thr Tyr Asn Thr Ile Ile Ser Arg
                 85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Lys Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Glu Lys Leu
465                 470                 475                 480
```

```
Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Ala Gly Ser Pro Asp Tyr Thr Asp Ile Lys Leu Ser Val
        515                 520                 525

Lys Cys Ala Gly Met Thr Asp Lys Ile Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Leu Val Asp Asp Thr Phe Thr Ile Lys Gln
            565                 570                 575

Thr

<210> SEQ ID NO 16
<211> LENGTH: 575
<212> TYPE: PRT
<213> ORGANISM: Bacillus phage phi29

<400> SEQUENCE: 16

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Glu Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270
```

```
Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 17
<211> LENGTH: 575
<212> TYPE: PRT
<213> ORGANISM: Bacillus phage phi29

<400> SEQUENCE: 17

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asn Leu Tyr Phe His Asn Leu Lys
    50                  55                  60

Phe Asp Gly Ala Phe Ile Ile Asn Trp Leu Glu Arg Asn Gly Phe Lys
65                  70                  75                  80
```

```
Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Asp Phe Lys Asp Ile Ile Thr Thr Lys Lys Phe Lys
            195                 200                 205

Lys Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Gly Tyr Pro Leu His Ile Gln His Ile
            275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495
```

```
Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 18
<211> LENGTH: 575
<212> TYPE: PRT
<213> ORGANISM: Bacillus phage phi29

<400> SEQUENCE: 18

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Glu Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300
```

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
            515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 19
<211> LENGTH: 575
<212> TYPE: PRT
<213> ORGANISM: Bacillus phage phi29

<400> SEQUENCE: 19

Met Lys His Met Pro Arg Lys Arg Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys

-continued

```
                100             105             110
Arg Lys Ile His Thr Val Ile Tyr Asp Ser Leu Lys Lys Leu Pro Phe
            115                 120                 125
Pro Val Lys Lys Ile Ala Lys Asp Phe Lys Leu Thr Val Leu Lys Gly
        130                 135                 140
Asp Ile Asp Tyr His Lys Glu Arg Pro Val Gly Tyr Lys Ile Thr Pro
145                 150                 155                 160
Glu Glu Tyr Ala Tyr Ile Lys Asn Asp Ile Gln Ile Ile Ala Glu Ala
                165                 170                 175
Leu Leu Ile Gln Phe Lys Gln Gly Leu Asp Arg Met Thr Ala Gly Ser
            180                 185                 190
Asp Ser Leu Lys Asp Phe Lys Asp Ile Ile Thr Thr Lys Lys Phe Lys
        195                 200                 205
Lys Val Phe Pro Thr Leu Ser Leu Gly Leu Asp Lys Lys Val Arg Tyr
    210                 215                 220
Ala Tyr Arg Gly Gly Phe Thr Trp Leu Asn Asp Arg Phe Lys Glu Lys
225                 230                 235                 240
Glu Ile Gly Glu Gly Thr Val Phe Asp Val Asn Ser Leu Tyr Pro Ala
                245                 250                 255
Gln Met Tyr Ser Arg Leu Leu Pro Tyr Gly Glu Pro Ile Val Phe Glu
            260                 265                 270
Gly Lys Tyr Val Trp Asp Glu Asp Tyr Pro Leu His Ile Gln His Ile
        275                 280                 285
Arg Cys Glu Phe Glu Leu Lys Glu Gly Tyr Ile Pro Thr Ile Gln Ile
    290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
        355                 360                 365
Tyr Ile Lys Thr Thr Ser Glu Gly Ala Ile Lys Gln Leu Ala Lys Leu
    370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
        435                 440                 445
Tyr Asp Arg Ile Ile Tyr Cys Asp Thr Asp Ser Ile His Leu Thr Gly
    450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Pro Lys Thr Tyr Ile Gln Asp Ile Tyr Met Lys Glu Val Asp Gly Glu
            500                 505                 510
Leu Val Glu Gly Ser Pro Asp Asp Tyr Thr Asp Ile Lys Leu Ser Val
        515                 520                 525
```

```
Lys Cys Ala Gly Met Thr Asp Lys Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 20
<211> LENGTH: 575
<212> TYPE: PRT
<213> ORGANISM: Bacillus phage phi29

<400> SEQUENCE: 20

Met Lys His Met Pro Arg Lys Arg Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Lys Val Phe Pro Thr Leu Ser Leu Gly Leu Asp Lys Lys Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
```

```
                    325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
            355                 360                 365
Tyr Ile Lys Thr Thr Ser Glu Gly Ala Val Lys Gln Leu Ala Lys Leu
            370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
            405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
            435                 440                 445
Tyr Asp Arg Ile Ile Tyr Cys Asp Thr Asp Ser Ile His Leu Thr Gly
            450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
            485                 490                 495
Pro Lys Thr Tyr Ile Gln Asp Ile Tyr Met Lys Glu Val Asp Gly Glu
            500                 505                 510
Leu Val Glu Gly Ser Pro Asp Asp Tyr Thr Asp Ile Lys Leu Ser Val
            515                 520                 525
Lys Cys Ala Gly Met Thr Asp Lys Ile Lys Lys Glu Val Thr Phe Glu
            530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
            565                 570                 575

<210> SEQ ID NO 21
<211> LENGTH: 575
<212> TYPE: PRT
<213> ORGANISM: Bacillus phage phi29

<400> SEQUENCE: 21

Met Lys His Met Pro Arg Lys Arg Tyr Ser Cys Asp Phe Glu Thr Thr
1               5                   10                  15
Thr Lys Val Glu Asp Cys Arg Val Trp Ala Tyr Gly Tyr Met Asn Ile
            20                  25                  30
Glu Asp His Ser Glu Tyr Lys Ile Gly Asn Ser Leu Asp Glu Phe Met
            35                  40                  45
Ala Trp Ala Leu Lys Val Gln Ala Asp Leu Tyr Phe His Asn Leu Lys
        50                  55                  60
Phe Asp Gly Ala Phe Thr Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
            85                  90                  95
Thr Gly Gln Trp Tyr Met Ile Asp Ile Cys Leu Gly Tyr Lys Gly Lys
            100                 105                 110
Arg Lys Ile His Thr Val Ile Tyr Asp Ser Leu Lys Lys Leu Pro Phe
            115                 120                 125
```

-continued

```
Pro Val Lys Lys Ile Ala Lys Asp Phe Lys Leu Thr Val Leu Lys Gly
130                 135                 140
Asp Ile Asp Tyr His Lys Glu Arg Pro Val Gly Tyr Lys Ile Thr Pro
145                 150                 155                 160
Glu Glu Tyr Ala Tyr Ile Lys Asn Asp Ile Gln Ile Ile Ala Glu Ala
                165                 170                 175
Leu Leu Ile Gln Phe Lys Gln Gly Leu Asp Arg Met Thr Ala Gly Ser
                180                 185                 190
Asp Ser Leu Lys Asp Phe Lys Asp Ile Ile Thr Thr Lys Lys Phe Lys
                195                 200                 205
Lys Val Phe Pro Thr Ser Ser Leu Gly Leu Asp Lys Lys Val Arg Tyr
210                 215                 220
Ala Tyr Arg Gly Gly Phe Thr Trp Leu Asn Asp Arg Phe Lys Glu Lys
225                 230                 235                 240
Glu Ile Gly Glu Gly Met Val Phe Asp Val Asn Ser Leu Tyr Pro Ala
                245                 250                 255
Gln Met Tyr Ser Arg Leu Leu Pro Tyr Gly Glu Pro Ile Val Phe Glu
                260                 265                 270
Gly Lys Tyr Val Trp Asp Glu Asp Tyr Pro Leu His Ile Gln His Ile
                275                 280                 285
Arg Cys Glu Phe Glu Leu Lys Glu Gly Tyr Ile Pro Thr Ile Gln Ile
290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Glu Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
                355                 360                 365
Tyr Ile Lys Thr Thr Ser Glu Gly Ala Ile Lys Gln Leu Ala Lys Leu
370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
                420                 425                 430
Ile Ala Ala Trp Ala Arg Tyr Thr Thr Ile Thr Ala Ala Gln Ala Cys
                435                 440                 445
Tyr Asp Arg Ile Ile Tyr Cys Asp Thr Asp Ser Ile His Leu Thr Gly
450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Lys
                500                 505                 510
Leu Ile Ala Gly Ser Pro Asp Asp Tyr Thr Asp Ile Lys Phe Ser Val
                515                 520                 525
Lys Cys Ala Gly Met Pro Asp Lys Ile Lys Glu Val Thr Phe Glu
530                 535                 540
Asn Phe Lys Val Gly Phe Ser Arg Lys Met Lys Pro Lys Pro Val Gln
```

```
                545                 550                 555                 560
            Val Pro Gly Gly Val Val Leu Val Asp Asp Thr Phe Thr Ile Arg
                            565                 570                 575

<210> SEQ ID NO 22
<211> LENGTH: 575
<212> TYPE: PRT
<213> ORGANISM: Bacillus phage phi29

<400> SEQUENCE: 22

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Glu Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350
```

```
Phe Lys Ala Thr Thr Gly Leu Phe Lys Asp Phe Ile Asp Lys Trp Thr
            355                 360                 365
Tyr Ile Lys Thr Thr Ser Glu Gly Ala Ile Lys Gln Leu Ala Lys Leu
370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
            435                 440                 445
Tyr Asp Arg Ile Ile Tyr Cys Asp Thr Asp Ser Ile His Leu Thr Gly
450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Pro Lys Thr Tyr Ile Gln Asp Ile Tyr Met Lys Glu Val Asp Gly Glu
            500                 505                 510
Leu Val Glu Gly Ser Pro Asp Asp Tyr Thr Asp Ile Lys Leu Ser Val
            515                 520                 525
Lys Cys Ala Gly Met Thr Asp Lys Ile Lys Lys Glu Val Thr Phe Glu
            530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
                565                 570                 575
```

<210> SEQ ID NO 23
<211> LENGTH: 575
<212> TYPE: PRT
<213> ORGANISM: Bacillus phage phi29

<400> SEQUENCE: 23

```
Met Lys His Met Pro Arg Lys Arg Tyr Ser Cys Asp Phe Glu Thr Thr
1               5                   10                  15
Thr Lys Val Glu Asp Cys Arg Val Trp Ala Tyr Gly Tyr Met Asn Ile
            20                  25                  30
Glu Asp His Ser Glu Tyr Lys Ile Gly Asn Ser Leu Asp Glu Phe Met
        35                  40                  45
Ala Trp Val Leu Lys Val Gln Ala Asp Leu Tyr Phe His Asn Leu Lys
50                  55                  60
Phe Asp Gly Ala Phe Ile Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
                85                  90                  95
Thr Gly Gln Trp Tyr Met Ile Asp Ile Cys Leu Gly Tyr Lys Gly Lys
            100                 105                 110
Arg Lys Ile His Thr Val Ile Tyr Asp Ser Leu Lys Lys Leu Pro Phe
        115                 120                 125
Pro Val Lys Lys Ile Ala Lys Asp Phe Lys Leu Thr Val Leu Lys Gly
130                 135                 140
Asp Ile Asp Tyr His Lys Glu Arg Pro Val Gly Tyr Lys Ile Thr Pro
145                 150                 155                 160
```

```
Glu Glu Tyr Ala Tyr Ile Lys Asn Asp Ile Gln Ile Ala Glu Ala
            165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
            195                 200                 205

Lys Val Phe Pro Thr Leu Ser Leu Gly Leu Asp Lys Lys Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
            245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
            290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Glu Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Gln Lys Thr Tyr Ile Gln Asp Ile Tyr Met Lys Glu Val Asp Gly Lys
            500                 505                 510

Leu Ile Ala Gly Ser Pro Asp Asp Tyr Thr Asp Ile Lys Phe Ser Val
            515                 520                 525

Lys Cys Ala Gly Met Pro Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Arg
            565                 570                 575
```

<210> SEQ ID NO 24
<211> LENGTH: 575
<212> TYPE: PRT
<213> ORGANISM: Bacillus phage phi29

<400> SEQUENCE: 24

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Lys Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Ala Phe Asp Val Asn Ser Leu Tyr Pro Ala
                245                 250                 255

Gln Met Tyr Asn Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380
```

```
Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Val Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
                500                 505                 510

Leu Ile Ala Gly Ser Pro Asp Asp Tyr Thr Asp Ile Lys Phe Ser Val
        515                 520                 525

Lys Cys Ala Gly Met Pro Asp Arg Ile Lys Lys Glu Val Thr Phe Glu
530                 535                 540

Asn Phe Lys Val Gly Phe Ser Arg Lys Met Arg Pro Lys Pro Val Gln
545                 550                 555                 560

Val Pro Gly Gly Val Val Leu Val Asp Asp Thr Phe Thr Ile Arg
                565                 570                 575

<210> SEQ ID NO 25
<211> LENGTH: 575
<212> TYPE: PRT
<213> ORGANISM: Bacillus phage phi29

<400> SEQUENCE: 25

Met Lys His Met Pro Arg Lys Arg Tyr Ser Cys Asp Phe Glu Ala Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Ala Leu Gln Val Gln Ala Asp Leu Tyr Phe His Asn Leu Lys
        50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
        130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
```

```
                    180                 185                 190
Asp Ser Leu Lys Asp Phe Lys Asp Ile Ile Thr Thr Lys Lys Phe Lys
        195                 200                 205
Lys Val Phe Pro Thr Leu Ser Leu Gly Leu Asp Lys Lys Val Arg Tyr
        210                 215                 220
Ala Tyr Arg Gly Gly Phe Thr Trp Leu Asn Asp Arg Phe Lys Glu Lys
225                 230                 235                 240
Glu Ile Gly Glu Gly Met Val Phe Asp Val Asn Ser Leu Tyr Pro Ala
                    245                 250                 255
Gln Met Tyr Ser Arg Leu Leu Pro Tyr Gly Glu Pro Ile Val Phe Glu
            260                 265                 270
Gly Lys Tyr Val Trp Asp Glu Asp Tyr Pro Leu His Ile Gln His Ile
        275                 280                 285
Arg Cys Glu Phe Glu Leu Lys Glu Gly Tyr Ile Pro Thr Ile Gln Ile
        290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                    325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
        355                 360                 365
Tyr Ile Lys Thr Thr Ser Glu Gly Ala Ile Lys Gln Leu Ala Lys Leu
        370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                    405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
        435                 440                 445
Tyr Asp Arg Ile Ile Tyr Cys Asp Thr Asp Ser Ile His Leu Thr Gly
        450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                    485                 490                 495
Pro Lys Thr Tyr Ile Gln Asp Ile Tyr Met Lys Glu Val Asp Gly Glu
            500                 505                 510
Leu Val Glu Gly Ser Pro Asp Asp Tyr Thr Asp Ile Lys Leu Ser Val
        515                 520                 525
Lys Cys Ala Gly Met Thr Asp Lys Ile Lys Lys Glu Val Thr Phe Glu
        530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
                    565                 570                 575

<210> SEQ ID NO 26
<211> LENGTH: 575
<212> TYPE: PRT
<213> ORGANISM: Bacillus phage phi29
```

<400> SEQUENCE: 26

```
Met Lys His Met Pro Arg Lys Arg Tyr Ser Cys Asp Phe Glu Ala Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Gln Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Lys Val Phe Pro Thr Leu Ser Leu Gly Leu Asp Lys Lys Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Ser Phe Lys Asp Phe Ile Asp Lys Trp Thr
        355                 360                 365

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
```

```
                 405                 410                 415
Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
            515                 520                 525

Lys Cys Ala Gly Met Thr Asp Lys Ile Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 27
<211> LENGTH: 575
<212> TYPE: PRT
<213> ORGANISM: Bacillus phage phi29

<400> SEQUENCE: 27

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205
```

Lys Val Phe Pro Thr Leu Ser Leu Gly Leu Asp Lys Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
            245                 250                 255

Gln Met Tyr Ser Arg Leu Leu Pro Tyr Gly Glu Pro Ile Val Phe Glu
        260                 265                 270

Gly Lys Tyr Val Trp Asp Glu Asp Tyr Pro Leu His Ile Gln His Ile
    275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
        340                 345                 350

Phe Lys Ala Thr Thr Gly Leu Phe Lys Asp Phe Ile Asp Lys Trp Thr
    355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Thr Lys Asp Pro Val Tyr Thr Pro Met Gly Val Phe
        420                 425                 430

Ile Thr Ala Trp Ala Arg Tyr Thr Thr Ile Thr Ala Ala Gln Ala Cys
    435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Pro Lys Thr Tyr Ile Gln Asp Ile Tyr Met Lys Glu Val Asp Gly Glu
        500                 505                 510

Leu Val Glu Gly Ser Pro Asp Asp Tyr Thr Asp Ile Lys Leu Ser Val
    515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
            565                 570                 575

<210> SEQ ID NO 28
<211> LENGTH: 575
<212> TYPE: PRT
<213> ORGANISM: Bacillus phage phi29

<400> SEQUENCE: 28

Met Lys His Met Pro Arg Lys Met Tyr Ser Cys Asp Phe Glu Thr Thr
1               5                   10                  15

```
Thr Lys Val Glu Asp Cys Arg Val Trp Ala Tyr Gly Tyr Met Asn Ile
             20                  25                  30

Glu Asp His Ser Glu Tyr Lys Ile Gly Asn Ser Leu Asp Glu Phe Met
         35                  40                  45

Ala Trp Ala Leu Lys Val Gln Ala Asp Leu Tyr Phe His Asn Leu Lys
 50                  55                  60

Phe Asp Gly Ala Phe Ile Ile Asn Trp Leu Glu Arg Asn Gly Phe Lys
 65                  70                  75                  80

Trp Ser Ala Asp Gly Leu Pro Asn Thr Tyr Asn Thr Ile Ile Ser Arg
                 85                  90                  95

Thr Gly Gln Trp Tyr Met Ile Asp Ile Cys Leu Gly Tyr Lys Gly Lys
             100                 105                 110

Arg Lys Ile His Thr Val Ile Tyr Asp Ser Leu Lys Lys Leu Pro Phe
             115                 120                 125

Pro Val Lys Lys Ile Ala Lys Asp Phe Lys Leu Thr Val Leu Lys Gly
         130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
             165                 170                 175

Leu Leu Ile Gln Phe Lys Gln Gly Leu Gly Arg Met Thr Ala Gly Ser
             180                 185                 190

Asp Ser Leu Lys Asp Phe Lys Asp Ile Ile Thr Thr Lys Lys Phe Lys
         195                 200                 205

Lys Val Phe Pro Thr Leu Ser Leu Gly Leu Asp Lys Lys Val Arg Tyr
     210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                 245                 250                 255

Gln Met Tyr Ser Arg Leu Leu Pro Tyr Gly Glu Pro Ile Val Phe Glu
             260                 265                 270

Gly Lys Tyr Val Trp Asp Glu Asp Tyr Pro Leu His Ile Gln His Ile
             275                 280                 285

Arg Cys Glu Phe Glu Leu Lys Glu Gly Tyr Ile Pro Thr Ile Gln Ile
             290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                 325                 330                 335

Lys Glu His Tyr Asp Leu Tyr Asn Val Glu Tyr Ile Ser Gly Leu Lys
             340                 345                 350

Phe Lys Ala Thr Thr Gly Leu Phe Lys Asp Phe Ile Asp Lys Trp Thr
         355                 360                 365

Tyr Ile Lys Thr Thr Ser Glu Gly Ala Ile Lys Gln Leu Ala Lys Leu
     370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                 405                 410                 415

Gly Glu Glu Glu Thr Lys Asp Pro Val Tyr Thr Pro Met Gly Val Phe
             420                 425                 430
```

```
Ile Thr Ala Trp Ala Arg Tyr Thr Ile Thr Ala Ala Gln Ala Cys
            435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
            515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 29
<211> LENGTH: 575
<212> TYPE: PRT
<213> ORGANISM: Bacillus phage phi29

<400> SEQUENCE: 29

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Lys Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240
```

Glu Ile Gly Glu Gly Met Val Phe Asp Val Asn Ser Leu Tyr Pro Ala
            245                 250                 255

Gln Met Tyr Ser Arg Leu Leu Pro Tyr Gly Pro Ile Val Phe Glu
        260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
        515                 520                 525

Lys Cys Ala Gly Met Thr Asp Lys Ile Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 30
<211> LENGTH: 575
<212> TYPE: PRT
<213> ORGANISM: Bacillus phage phi29

<400> SEQUENCE: 30

Met Lys His Met Pro Arg Lys Arg Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met

```
            35                  40                  45
Ala Trp Ala Leu Lys Val Gln Ala Asp Leu Tyr Phe His Asn Leu Lys
 50                  55                  60

Phe Asp Gly Ala Phe Ile Ile Asn Trp Leu Glu Arg Asn Gly Phe Lys
 65                  70                  75                  80

Trp Ser Ala Asp Gly Leu Pro Asn Thr Tyr Asn Thr Ile Ile Ser Arg
                 85                  90                  95

Thr Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
            130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
            195                 200                 205

Lys Val Phe Pro Thr Leu Ser Leu Gly Leu Asp Lys Lys Val Arg Tyr
210                 215                 220

Ala Tyr Arg Gly Gly Phe Thr Trp Leu Asn Asp Arg Ser Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Gly Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460
```

```
Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Pro Lys Thr Tyr Ile Gln Asp Ile Tyr Met Lys Glu Val Asp Gly Glu
        500                 505                 510

Leu Val Glu Gly Ser Pro Asp Asp Tyr Thr Asp Ile Lys Leu Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575
```

<210> SEQ ID NO 31
<211> LENGTH: 575
<212> TYPE: PRT
<213> ORGANISM: Bacillus phage phi29

<400> SEQUENCE: 31

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Ala Leu Lys Val Gln Ala Asp Leu Tyr Phe His Asn Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
        130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Lys Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
```

```
                260                 265                 270
Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 32
<211> LENGTH: 575
<212> TYPE: PRT
<213> ORGANISM: Bacillus phage phi29

<400> SEQUENCE: 32

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60
```

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
            85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
            130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
            195                 200                 205

Lys Val Phe Pro Thr Leu Ser Leu Gly Leu Asp Lys Lys Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
            290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg

```
                    485                 490                 495
Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
            515                 520                 525

Lys Cys Ala Gly Met Thr Asp Lys Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 33
<211> LENGTH: 575
<212> TYPE: PRT
<213> ORGANISM: Bacillus phage phi29

<400> SEQUENCE: 33

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Glu Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Lys Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285
```

```
Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
                355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Glu Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Ala Arg Tyr Thr Thr Ile Thr Ala Ala Gln Ala Cys
                435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
                500                 505                 510

Leu Val Glu Gly Ser Pro Asp Asp Tyr Thr Asp Ile Lys Leu Ser Val
                515                 520                 525

Lys Cys Ala Gly Met Thr Asp Lys Ile Lys Lys Glu Val Thr Phe Glu
                530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 34
<211> LENGTH: 575
<212> TYPE: PRT
<213> ORGANISM: Bacillus phage phi29

<400> SEQUENCE: 34

Met Lys His Met Pro Arg Lys Arg Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
                35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95
```

```
Met Gly Gln Trp Tyr Met Ile Asp Ile Cys Ser Gly Tyr Lys Gly Lys
            100                 105                 110

Arg Lys Ile His Thr Val Ile Tyr Asp Ser Ser Lys Lys Leu Pro Phe
            115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Val Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
            210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Lys
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
            290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Ala Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Glu Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Lys
            500                 505                 510
```

```
Leu Val Glu Gly Ser Pro Asp Asp Tyr Thr Asp Ile Lys Leu Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Arg Met Lys Pro Lys Pro Val Gln
545                 550                 555                 560

Val Pro Gly Gly Val Val Leu Val Asp Asp Thr Phe Thr Ile Lys
            565                 570                 575

<210> SEQ ID NO 35
<211> LENGTH: 575
<212> TYPE: PRT
<213> ORGANISM: Bacillus phage phi29

<400> SEQUENCE: 35

Met Lys His Met Pro Arg Lys Arg Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Ala Val Ile Tyr Asp Ser Ser Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320
```

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Arg Arg Ala Lys Tyr Leu Arg
            485                 490                 495

Gln Lys Thr Tyr Ile Gln Asp Ile Tyr Met Lys Glu Val Asp Gly Lys
            500                 505                 510

Leu Ile Ala Gly Ser Pro Asp Asp Tyr Thr Asp Ile Lys Phe Ser Val
            515                 520                 525

Lys Cys Ala Gly Met Pro Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
            565                 570                 575

<210> SEQ ID NO 36
<211> LENGTH: 575
<212> TYPE: PRT
<213> ORGANISM: Bacillus phage phi29

<400> SEQUENCE: 36

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
            35                  40                  45

Ala Trp Ala Leu Lys Val Gln Ala Asp Leu Tyr Phe His Asn Leu Lys
        50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
            85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe

-continued

```
            115                 120                 125
Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Asp Phe Lys Asp Ile Ile Thr Thr Lys Lys Phe Lys
            195                 200                 205

Lys Val Phe Pro Thr Leu Ser Leu Gly Leu Asp Lys Lys Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
                260                 265                 270

Gly Lys Tyr Ala Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
                500                 505                 510

Leu Val Glu Gly Ser Pro Asp Asp Tyr Thr Asp Ile Lys Leu Ser Val
            515                 520                 525

Lys Cys Ala Gly Met Thr Asp Lys Ile Lys Lys Glu Val Thr Phe Glu
530                 535                 540
```

```
Asn Phe Lys Val Gly Phe Ser Arg Lys Met Lys Pro Lys Pro Val Gln
545                 550                 555                 560

Val Pro Gly Gly Val Leu Val Asp Asp Thr Phe Thr Ile Lys
            565                 570                 575
```

<210> SEQ ID NO 37
<211> LENGTH: 575
<212> TYPE: PRT
<213> ORGANISM: Bacillus phage phi29

<400> SEQUENCE: 37

```
Met Lys His Met Pro Arg Lys Arg Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
        50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Ser Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Ser Lys Lys Leu Pro Phe
            115                 120                 125

Pro Val Lys Lys Ile Ala Lys Asp Phe Lys Leu Thr Val Leu Lys Gly
        130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Val Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
```

```
                340             345             350
Phe Glu Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
            515                 520                 525

Lys Cys Ala Gly Met Thr Asp Lys Ile Lys Lys Glu Val Thr Phe Glu
        530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 38
<211> LENGTH: 575
<212> TYPE: PRT
<213> ORGANISM: Bacillus phage phi29

<400> SEQUENCE: 38

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140
```

-continued

```
Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Lys Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
                500                 505                 510

Leu Val Glu Gly Ser Pro Asp Asp Tyr Thr Asp Ile Lys Leu Ser Val
            515                 520                 525

Lys Cys Ala Gly Met Thr Asp Lys Ile Lys Lys Glu Val Thr Phe Glu
        530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
```

<210> SEQ ID NO 39
<211> LENGTH: 575
<212> TYPE: PRT
<213> ORGANISM: Bacillus phage phi29

<400> SEQUENCE: 39

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Ala Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
        195                 200                 205

Lys Val Phe Pro Thr Leu Ser Leu Gly Leu Asp Lys Lys Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365
```

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
        515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 40
<211> LENGTH: 575
<212> TYPE: PRT
<213> ORGANISM: Bacillus phage phi29

<400> SEQUENCE: 40

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Ala Leu Lys Val Gln Ala Asp Leu Tyr Phe His Asn Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Thr Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
            130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

```
Leu Leu Ile Gln Phe Lys Gln Gly Leu Asp Arg Met Thr Ala Gly Ser
            180                 185                 190

Asp Ser Leu Lys Asp Phe Lys Asp Ile Ile Thr Thr Lys Lys Phe Lys
            195                 200                 205

Lys Val Phe Pro Thr Leu Ser Leu Gly Leu Asp Lys Lys Val Arg Tyr
            210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
            290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Pro Lys Thr Tyr Ile Gln Asp Ile Tyr Met Lys Glu Val Asp Gly Glu
            500                 505                 510

Leu Val Glu Gly Ser Pro Asp Asp Tyr Thr Asp Ile Lys Leu Ser Val
            515                 520                 525

Lys Cys Ala Gly Met Thr Asp Lys Ile Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
            565                 570                 575
```

PHI29 DNA POLYMERASE MUTANTS HAVING INCREASED THERMOSTABILITY AND PROCESSIVITY

This application is a divisional of U.S. application Ser. No. 14/135,860, filed Dec. 20, 2013, which claims the benefit of U.S. Application Ser. No. 61/815,893, filed Apr. 25, 2013, each of which is expressly incorporated by reference herein in its entirety.

Mutants and methods utilizing such mutants, of bacteriophage phi29 DNA polymerase (phi29 DNA polymerase mutants). Such mutants have increased thermostability and result in increased processivity.

Bacteriophage phi29 DNA polymerase is a monomeric enzyme of 66 kDa, a protein-primed DNA-dependent replicase belonging to the eukaryotic-type family of DNA polymerases (family B) (Bernad et al., 1987). Like other DNA polymerases, it accomplishes DNA synthesis by adding nucleotides to the 3'-OH group of growing DNA chain with insertion discrimination values ranging from $10^4$ to $10^6$ (Esteban et al., 1993). It contains AN exonuclease domain that catalyzes 3'→5' exonucleolysis of mismatched nucleotides. This proofreading feature enhances replication fidelity $10^2$-fold (Esteban et al., 1994).

Phi29 DNA polymerase has distinctive functional features when compared to other replicases. (1) In vivo, it can initiate DNA synthesis by adding dAMP onto the hydroxyl group of $Ser^{232}$ of phage terminal protein (TP) (Salas & da Vega 2006). (2) Unlike most replicases that rely on accessory proteins to be stably bound to the DNA, phi29 DNA polymerase itself has very strong binding capacity to single stranded DNA, and performs DNA synthesis without processivity factors, accounting for the highest known processivity (>70 kb) among other DNA polymerases (Blanco et al., 1989). (3) It unwinds the parental DNA helix, using dNTP cleavage energy for DNA polymerization that accompanies DNA unwinding and enabling it to replicate the double-stranded genome without any unwinding protein.

Compared with the structure of other family B DNA polymerases, phi 29 DNA polymerase shows a common (right hand) fold containing palm, thumb and fingers subdomains (Kamtekar et al., 2004). The main structural difference between phi29 DNA polymerase and family B DNA polymerases is the presence of two additional subdomains, called TPR1 and TPR2 that are insertions between the fingers and palm subdomains (Dufour et al., 2000). TPR2 helps to form a narrow tunnel around the downstream DNA, forcing separation of the second strand before its entry into polymerase active site (Rodriguez et al. 2005). Additionally palm, thumb, TPR1, and TPR2 form a doughnut-shaped structure around the upstream duplex product, providing maximal DNA-binding stability which potentially enhances processivity in a manner analogous to sliding-clamp proteins (Berman et al. 2007). Such structural peculiarity provides high processivity and strand displacement activity which enables phi29 DNA polymerase to be used in isothermal multiple displacement amplification (MDA) (Dean et al. 2002), or rolling circle amplification (RCA) (Lizardi et al. 1998).

Amplification technologies based on phi29 DNA polymerase have several advantages compared to classical PCR DNA amplification methods. Any DNA sample can be amplified, because no sequence information is required; instead, random hexamer primers are used for DNA synthesis initiation. Amplicons synthesized by the phi29 DNA polymerase can be much larger comparing to those obtained by PCR. Isothermal DNA amplification reactions do not require special laboratory equipment such as thermal cyclers. These advantages make phi29 DNA polymerase suitable for detection and analysis of known and unknown circular viral genomes (Johne et al. 2009), replication of pathogenic plasmids (Hutchison et al. 2005), amplification of very small DNA samples, e.g. replication from filter paper blood spot samples, and for the description of new metagenomes. The ability to use small circular DNA samples (padlock probes) can be applied for generation of periodic DNA nanotemplates (Simmel et al. 2005) or RNA detection (Lagunavicius et al. 2010). High processivity, strong strand displacement activity, and high accuracy allow the enzyme to amplify whole genomes with minimal amplification bias or allele dropout (Lasken et al. 2003; Weissman et al. 2008) compared to PCR based whole genome amplification (WGA) methods, such as degenerate oligonucleotide polymerization (DOP-PCR) or primer extension polymerization (PEP-PCR) reaction. The stability of the phi29 DNA polymerase-DNA complex makes phi29 DNA polymerase attractive for single-molecule techniques. Phi29 DNA polymerase-DNA complexes are stable when captured in an electric field across the α-hemolysin nanopore, and can be used to study nucleic acid by drawing through the nanopore lumen during replication (Akeson et al. 2010).

For applications such as those described, the ability to perform reactions at increased temperature would be advantageous so that amplification reaction kinetics would be faster. Phi29 DNA polymerase is a typical mezophilic enzyme with an optimal reaction temperature of 30° C. A 30° C. reaction temperature may cause problems during amplification of DNA with high G/C content. Elevated reaction temperatures could improve DNA amplification efficiency and decrease formation of template-independent, non-specific reaction products in the whole genome amplification (WGA) reaction (Alsmadi et al. 2009). The 30° C. relatively low working temperature of phi29 DNA polymerase limits its application; a more thermostable enzyme could be used in many more DNA amplification techniques, generate more product, work faster, and increase amplification reaction sensitivity.

Attempts to improve phi29 DNA polymerase characteristics were performed. Amino acid mutations were inserted, or the phi29 DNA polymerase was fused with DNA binding motifs (de Vega et al. 2010). In determining the nucleotide base sequence of a DNA molecule, non-natural phi29 DNA polymerase was used in which the amino acid moiety at position 12, 14, or 16 of the polymerase was replaced by alanine, which resulted in reduced exonuclease activity, retaining DNA polymerase activity unchanged (U.S. Pat. No. 5,198,543). Reagents and phi29 DNA polymerase modifications were described that increase residence times for nucleotide analogues, for use in analytical operations such as nucleic acid sequence analysis and determination (EP2089517A2). A modified phi29 DNA polymerase was generated to obtain more efficient incorporation of labeled nucleotides used to generate FRET signal upon incorporation (WO2009091847A2). Typically, the FRET donor is linked to the polymerase, and the FRET acceptor is attached to the incoming nucleotide. FRET emission occurs when the polymerase binds to the incoming nucleotide and the FRET donor is brought into close proximity with the FRET acceptor. Incorporated nucleotides can be identified by emission spectrum of the FRET acceptor. Such strategy can be used in single-molecule sequencing reaction. A modified phi29 DNA polymerase with increased resistance to photodamage was described (U.S. Patent Publication No. 2010009355); the method changed amino acid moieties susceptible to photodamage to less sensitive amino acids. Photodamage resistance is very important in analysis systems using optical labels, e.g., single-molecule sequencing reaction. Prolonged exposure of chemical and biochemical reactants to radiation energy during excitation and detection of optical labels can damage polymerase by oxidizing sensitive amino acid moieties.

The inventive phi29 DNA polymerase mutants have increased protein stability and increased half-life, compared to wild type DNA polymerase. They are more stable in reaction mixtures with or without DNA. The inventive phi29 DNA polymerase mutants generate more amplification product. The inventive phi29 DNA polymerase mutants amplify genomic DNA with less bias compared to wild type DNA polymerase.

BRIEF DESCRIPTION OF THE DRAWINGS

FIG. 1 shows substitutions of amino acid residues in selected clones.

FIG. 2 shows CLUSTALW alignment of 30 selected protein sequences (SEQ ID NOS 10-40, respectively, in order of appearance).

FIG. 6 compares coverage evenness between wild-type and mutant variants of phi29 DNA polymerase.

FIG. 7 compares CG content between after whole genome analysis (WGA) between wild-type and mutant variants of phi29 DNA polymerase.

FIG. 8 compares DNA binding between of wild-type and mutant variants of phi29 DNA polymerase.

Figure 3A:
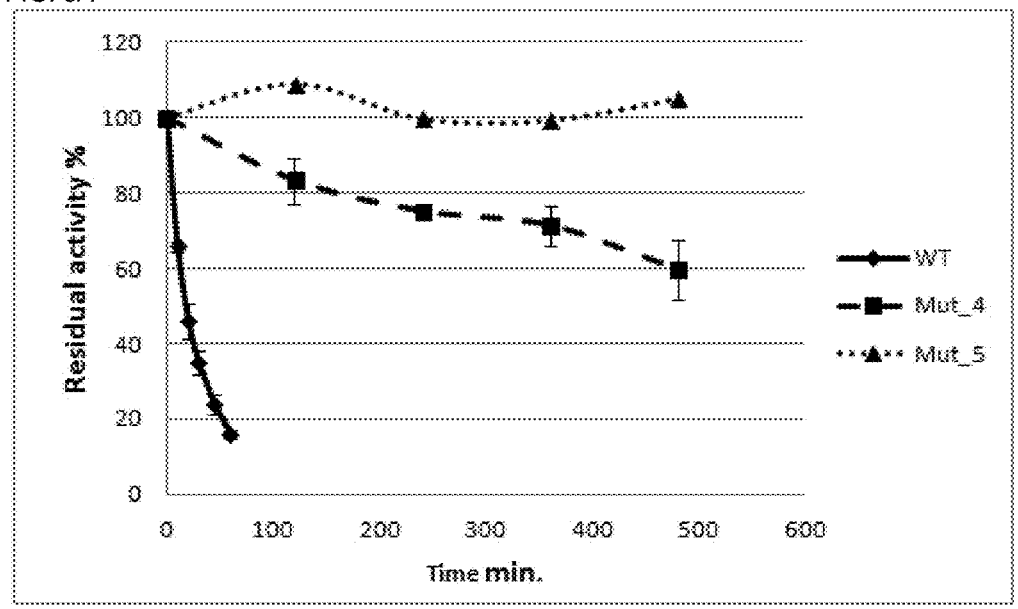
FIGS. 3A-F compare half-life ($T_{1/2}$) activities between wild-type and mutant variants of phi29 DNA polymerase.
Figure 3B:
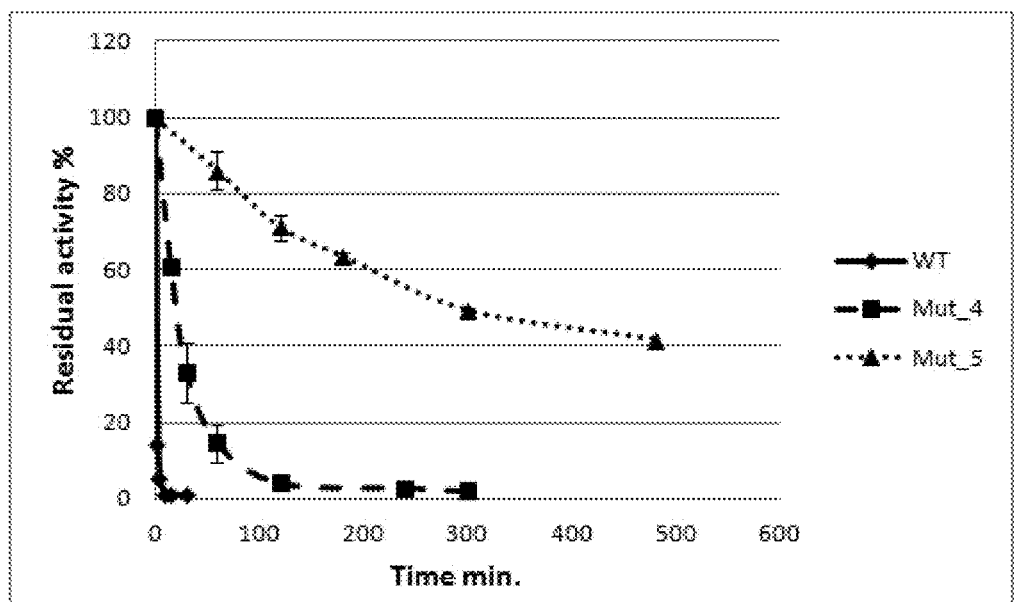

Random mutagenesis of wild type phi29 DNA polymerase gene was performed and a mutant library was created. Phi29 DNA polymerase mutants were selected using modified compartmentalized self replication (CSR) scheme. Multiple displacement amplification (MDA) reaction was used to screen a mutant library of phi29 DNA polymerase to find enzymes that were more thermostable and catalytically faster. Seven screening rounds were performed by increasing the reaction temperature from 40° C. to 50° C. and by shortening the reaction time from 16 hours to 4 hours. Selected clones of randomly mutated phi29 DNA polymerase were sequenced and analyzed. Sequencing data revealed possible mutations with a stabilizing effect on the phi29 DNA polymerase protein and enabled enzymatic activity at higher temperatures compared to wild type enzyme.

FIG. 1 shows substitutions of amino acids found in selected clones. Twelve most frequently found mutations were identified, these were M8R; V51A; M97T; L123S; G197D, K209E; E221K; E239G; Q497P; K512E; E515A; F526L.

Figure 2:
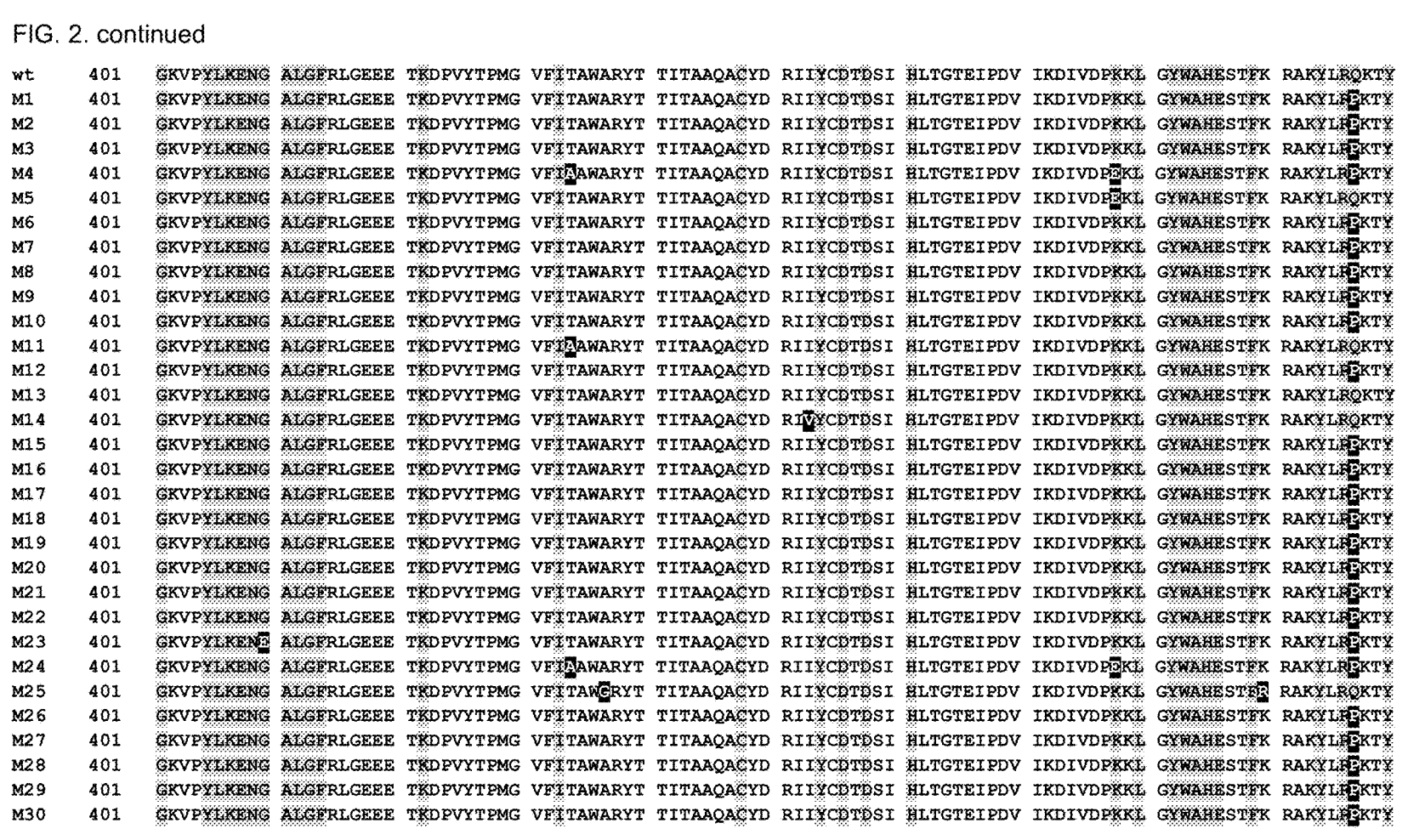

FIG. 2 shows multiple sequence alignment, using Clustalw, of 30 wild type and mutant proteins sequences. As is known in the art, such alignment identifies regions of similarity that may be a consequence of functional, structural, or evolutionary relationship. The wild-type sequence of phi29 DNA polymerase, denoted as wt, is given as a first sequence. The mutations are marked using white font color in a black background. The amino acids positions, mutations of which provided improved properties of phi29 DNA polymerase as known in the art, are marked as columns of amino acids (black font) highlighted in grey. The mutations originating from the presently disclosed selection and located in grey columns indicate that the inventive selection procedure targeted precisely the beneficial hot spot or even the exact amino acid change described elsewhere. Amino acids positions and references are:

T15, C22, N62, K132, K135, D169, V250, Y254, P255, C290, L351, K371, E375, A377, K379, Q380, K383, L384, N387, S388, C448, D456, D458, K478, E486, K512, K525, C530 referenced in WO 2009091847A2;

N62, K135, T368, E375, E486, K512 referenced in EP 1963536A2;

K135, T368, T372, K478, L480, K512 referenced in EP 2089517A2;

K64, F69, I70, I71, N72, W73, L74, E75, R76, T92, Y101, F128, K143, P153, I179, Q183, M188, T189, G191, F198, F211, R236, D249, N251, L253, Y254, P255, Y259, Q303, K305, N313, F360, F363, D365, T368, I370, K371, T372, T373, S374, E375, G376, A377, I378, K379, Q380, L381, A382, K383, L384, M385, L386, N387, S388, L389, Y390, G391, K392, F393, A394, S395, N396, P397, K402, Y405, L406, K407, E408, N409, G410, A411, L412, G413, F414, K422, I433, D458, K478, L480, A484, E486, R496, Q497, Y500, I504, K507, E508, V509, D510, G511, K512, L513, V514, C529, A531, G532, T534, K538, K555, P558, Q560, V561, P562, G563, G564, D570, F572, I574, K575 referenced in US 20100112645A1; and N62, F128, F230, W232, M246, F248, Y254, P300, Y315, F363, W367, T368, Y369, I378, M385, Y454, H461, Y482, W483, H485, F489, Y494, Y500, Y505, M506, Y521, F526 referenced in US 20100093555A1.

The described mutants increased protein stability. The mutant phi29 DNA polymerases performed at elevated temperatures, defined as temperatures exceeding 30° C. and had increased stability, defined in reaction mixtures without substrate.

The described mutants exhibited faster and more efficient DNA synthesis. This resulted in shorter time of DNA synthesis, generation of more product, and increased sensitivity threshold.

The described mutants increase phi29 DNA polymerase and DNA complex stability, due to increased affinity to DNA substrate.

The described mutants increased processivity. The mutants exhibited higher affinity to DNA and higher reaction velocity, which could synthesize more product without dissociating from DNA.

The described mutants exhibited unbiased whole genome amplification. Elevating the temperature of WGA reactions might result in less amplification bias, by eliminating the impact of GC content differences.

The described mutants exhibited resistance to inhibitors. Due to its stabilizing effect on phi29 DNA polymerase, the mutants may increase resistance to inhibitors such as heparin, formamide, guanidine hydrochloride, and/or photooxidative damage.

The described mutants exhibited increased accuracy; higher DNA polymerase fidelity is likely to occur with increased phi29 DNAP-DNA complex stability and processivity.

In one embodiment, phi29 DNA polymerase variants contained any single mutation among M8R; V51A; M97T; L123S; G197D; K209E; E221K; E239G; Q497P; K512E; E515A; F526L, or any combination of mutations among M8R; V51A; M97T; L123S; G197D; K209E; E221K; E239G; Q497P; K512E; E515A; F526L. In one embodiment, Mut_4 comprises five of these 12 mutations: M8R, V51A, M97T, G197D, E221K. In one embodiment, Mut_5 comprises eight of these 12 mutations: M8R, V51A, M97T, G197D, E221K, Q497P, K512E, F526L. The invention includes use of these mutations, either singly or in combination.

The following non-limiting examples illustrative use of the mutants and methods.

EXAMPLE 1

Selection of Thermostable and Faster Phi29 DNA Polymerase Mutants

A selection scheme of thermostable and faster phi29 DNA polymerase was based on compartmentalized self replication (CSR) strategy (Ghadessy et al. 2001) with modifications.

The wild-type phi29 DNA polymerase gene was mutated using error prone PCR. The mutated gene library was transformed into *Escherichia coli* ER2566 cells and phi29 DNA polymerase was expressed. Induced *E. coli* cells overexpressing mutant polymerases were washed two times with 1×Tango buffer and 0.5 mg/ml lyzozyme was added. The suspension was incubated for five min at room temperature.

Transformed Cells and Other Reaction Components were Emulsified Using the Following Protocol:

About 0.3 ml CSR mix containing 1×Tango buffer (330 mM Tris-acetate (pH 7.9 at 25° C.), 100 mM Mg-acetate, 660 mM K-acetate, 1 mg/ml BSA), 25 µM Exo-resistant random primer mix (5'-NpNpNpNpNp$^s$Np$^s$N-3'), 0.3 µM of primers no. 1 (5'-CAG CTG CAT TAA TGA ATC GGC CAAp$^s$Cp$^s$G-3') (SEQ ID NO: 1) and no. 2 (5'-TTA GCA GCC GGA TCT CAGp$^s$Tp$^s$G-3')(SEQ ID NO: 2), 1 mM dNTPs, and 1×10$^7$ of induced *E. coli* cells overexpressing mutant polymerases were added to 0.7 ml of oil phase containing 2% (vol/vol) ABIL EM 90, 0.055 (vol/vol) Triton X-100 in mineral oil under constant stirring (1714 rpm) at +4° C. (p$^s$=phosphorothioate), After addition of the aqueous phase (gradually over two min), stirring continued for five min. The emulsion was then frozen at −80° C. and thawed at 37° C.-50° C. (temperature was increased gradually after each selection round), Five freezing-thawing cycles were performed. The emulsion was then incubated for 16-2 hours (incubation time was reduced gradually after each selection round).

After Incubation the Aqueous Phase was Extracted Using Following Protocol:
1. Transfer 400 µl of emulsion to 1.5 ml tube and incubate at 75° C. for 10 min and centrifuge for three min at 13 000 rpm at room temperature, dispose of the upper (oil) phase.
2. Add 700 µl of water-saturated diethyl ether, vortex the tube, centrifuge for one min at 13 000 rpm and dispose of the upper (solvent) phase.
3. Add 750 µl of water-saturated ethyl-acetate, vortex the tube, centrifuge for one min at 13 000 rpm and dispose of the upper (solvent) phase.
4. Repeat step 2,
5. Remove residual solvent from the broken emulsion by centrifuging under vacuum for ten min at 37° C.

DNA was Extracted from Aqueous Phase Using Following Protocol:
1. Add an equal volume of phenol/chloroform (1:1) solution to the aqueous phase, vortex and centrifuge for five min at 13 000 rpm.
2. Remove the aqueous phase into a fresh tube and add an equal volume of chloroform, vortex and centrifuge for five min at 13 000 rpm.
3. Remove the aqueous phase into a fresh tube and add a 0.1 volume of 3 M sodium acetate, pH 5.2, to the aqueous phase and then 2.5 volumes of absolute ethanol. Incubate at −20° C. overnight or for 30-60 min, centrifuge for ten min at 13 000 rpm.
4. Remove the supernatant and add 180 µl 70% (v/v) ethanol, centrifuge for two min at 13 000 rpm.
5. Remove the supernatant and dry the pellet at room temperature. Dissolve pellet in 37 µl of 1×Fast Digest buffer (Thermo Fisher Scientific).

After chloroform/phenol extraction and ethanol precipitation *E. coli* genomic DNA was digested and MDA product was linearized by adding 1.5 µl of FD DpnI and FD AlwNI restriction endonucleases. The reaction mixture was incubated for 30 min at 37° C. and five min at 65° C.

Selection products were amplified with primers no. 3 (5'-GCG AGC CCG ATC TTC CCC ATC G-3') (SEQ ID NO: 3) and no. 4 (5'-TTA GCA GCC GGA TCT CAG TG-3') (SEQ ID NO: 4). After amplification PCR products that contained mutated phi29 DNA polymerase genes were re-cloned and transformed into *Escherichia coli* ER2566 cells for successive selection rounds.

EXAMPLE 2

Measurement of Half Life ($T_{1/2}$) of Phi29 DNA Polymerase Mutants

Increased protein thermostability was evaluated by measuring enzyme half-life ($T_{1/2}$) of activity at a particular temperature. A longer half-life indicated a more stable enzyme.

Two mutant variants of phi29 DNA polymerase were constructed. Mut_4 variant of phi DNA polymerase contains 5 mutations (M8R, V51A, M97T, G197D, E221K), these have never been characterized before. Mut_5 variant of phi29 DNA polymerase contains 8 most frequently (FIGS. 1 and 2) selected amino acids replacements (M8R, V51A, M97T, G197D, E221K, Q497P, K512E, F526L). Five mutations are the same as in Mut_4 enzyme (underlined mutations). Three additionally introduced mutations are known (U.S. Publication Nos. 2010009355A1, 20100112645A1, and EP2089517A2); those are also important for improved properties of phi29 DNA polymerase. Wild-type and mutant variants of phi29 DNA polymerase were purified to more than 95% protein homogeneity using five ion-exchange chromatography stages. The thermostability of wild-type, Mut_4 and Mut_5 enzymes without and with substrate was measured at 30° C., 37° C., and 40° C.

In this example, the half life ($T_{1/2}$) of different phi29 DNA polymerases without substrate was determined using the following protocol.

1. Prepare the following reaction mixture:

|  | For 1 assay | For 10 assays |
|---|---|---|
| 10x phi29 buffer | 4 µl | 40 µl |
| H$_2$O | 35 µl | 350 µl |
| phi29 DNA polymerase (100 ng/µl) | 1 µl | 10 µl |
| Total | 40 µl | 400 µl |

(10x phi29 buffer: 330 mM Tris-acetate, pH 7.9, 100 mM Mg-acetate, 660 mM K-acetate, 1%(v/v) Tween 20, 10 mM DTT)

2. Incubate samples at the appropriate temperature for 0 h-16 h (control samples which are incubated for 0 hours refers to 100% of activity).
3. After incubation, transfer samples to an ice bath and add 10 µl solution A.

| Solution A | For 1 assay | For 10 assays |
|---|---|---|
| 10 x phi29 buffer | 1 µl | 10 µl |
| Exo-Resistant random primer (500 µM) | 2.5 µl | 25 µl |
| dNTP mix (10 mM) | 5 µl | 50 µl |
| dCTP-$^3$H (37 µM) | 0.25 µl | 2.5 µl |
| Bacteriophage M13 single stranded plasmid DNA (0.805 mg/ml) | 1.25 µl | 12.5 µl |
| Total | 10 µl | 100 µl |

4. Incubate samples at 30° C. for 10 min
5. Stop reaction by adding 5 µl EDTA (0.5 M)
6. Transfer 40 µl of reaction mixture on the DE-81 filter paper (1.5×1.5 cm).
7. Dry papers
8. Wash papers three times with 7.5% Na$_2$HPO$_4$×10 H$_2$O
9. Wash once with distilled water
10. Dry papers
11. Transfer papers into vials with scintillator and measure cpm. Residual activity is calculated using the following formula:

Residual activity (%)=[*cpm* (sample)–*cpm* (blank)]
*100%/[*cpm* (control sample)–*cpm* (blank)].

The half life (T$_{1/2}$) of different phi29 DNA polymerases with substrate was determined using the following protocol:
1. Prepare the following reaction mixture:

|  | For 1 assay | For 10 assays |
|---|---|---|
| 10 x phi29 buffer | 4.45 µl | 44.5 µl |
| Bacteriophage M13 single stranded plasmid DNA (0.805 mg/ml) | 1.25 µl | 12.5 µl |
| Exo-Resistant random primer (500 µM) | 2.5 µl | 25 µl |
| H$_2$O | 35 µl | 350 µl |
| phi29 DNA polymerase (100 ng/µl) | 1 µl | 10 µl |
| Total: | 44.2 µl | 442 µl |

(10x phi29 buffer: 330 mM Tris-acetate, pH 7.9, 100 mM Mg-acetate, 660 mM K-acetate, 1%(v/v) Tween 20, 10 mM DTT)

2. Incubate samples at the appropriate temperature for 0 h-16 h (Control samples which are incubated for 0 hours refers 100% activity).
3. After incubation transfer samples to ice bath and add 5.8 µl solution B.

| Solution B | For 1 assay | For 10 assays |
|---|---|---|
| 10 x phi29 buffer | 0.55 µl | 5.5 µl |
| dNTP mix (10 mM) | 5 µl | 50 µl |
| dCTP-$^3$H (37 µM) | 0.25 µl | 2.5 µl |
| Total | 5.8 µl | 58 µl |

4. Incubate samples at 30° C. for ten min.
5. Stop reaction by adding 5 µl of EDTA (0.5 M).
6. Transfer 40 µl reaction mixture on the DE-81 filter paper (1.5×1.5 cm).
7. Dry papers
8. Wash papers three times with 7.5% Na$_2$HPO$_4$×10 H$_2$O.
9. Wash once with distilled water
10. Dry papers
11. Transfer papers into vials with scintillator and measure cpm. Residual activity is calculated using the following formula:

Residual activity (%)=[*cpm* (sample)–*cpm* (blank)]
*100%/[*cpm* (control sample)–*cpm* (blank)].

Figure 3C:
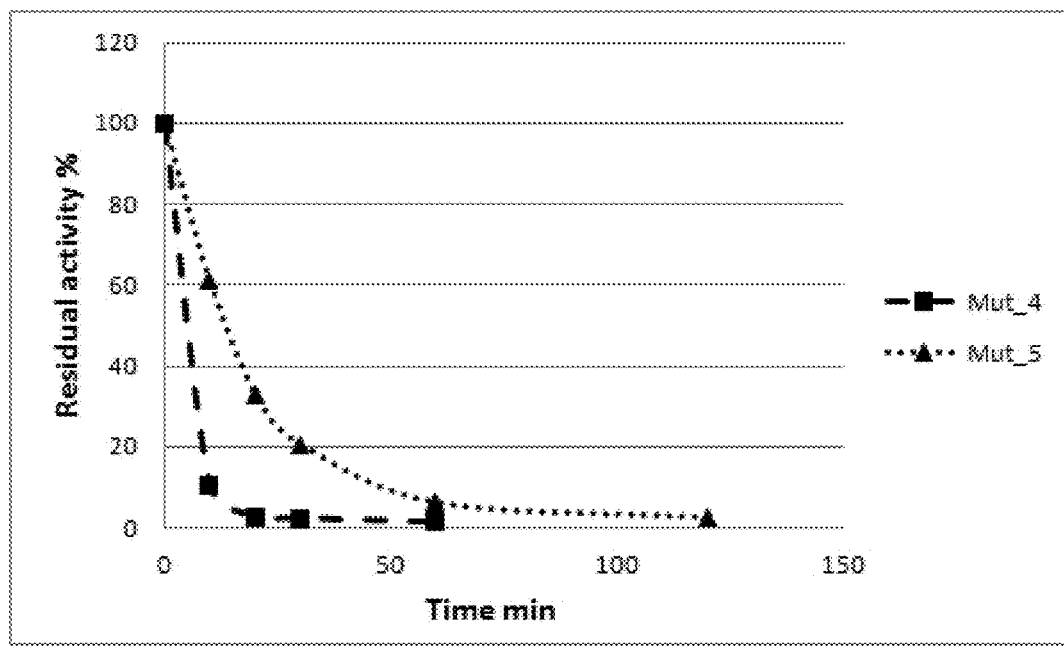
Figure 3D:
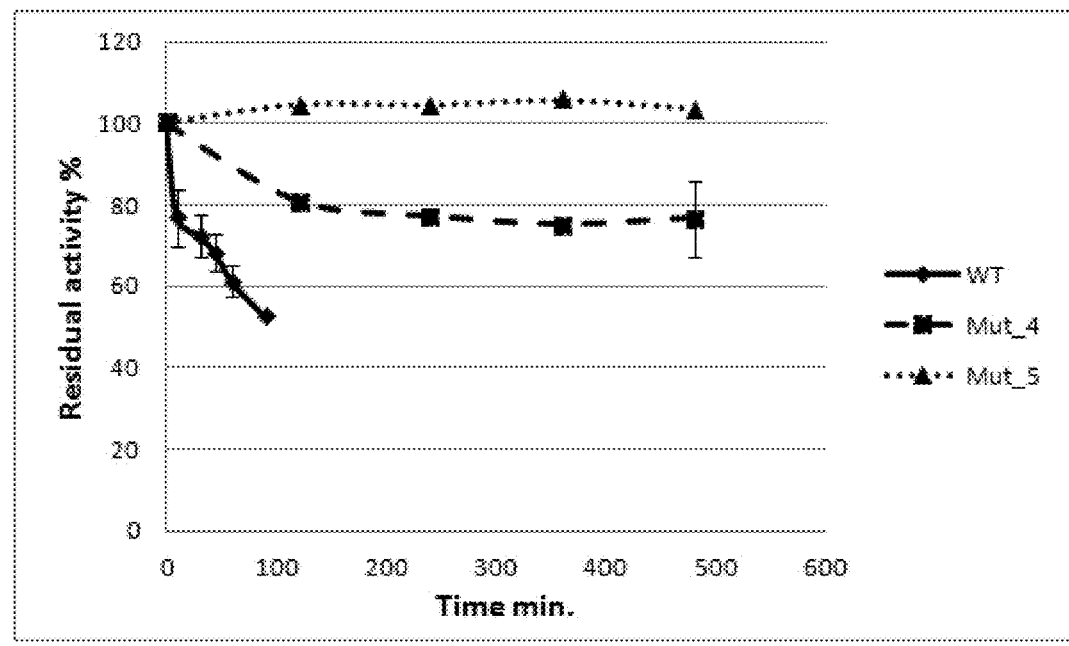
Figure 3E:
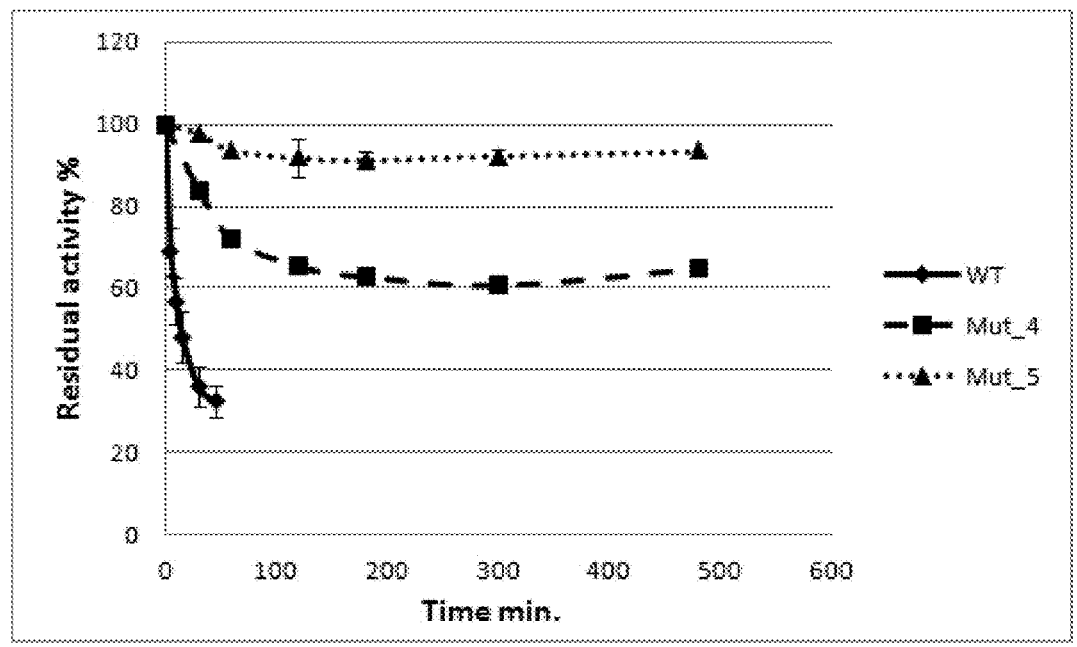
Figure 3F:
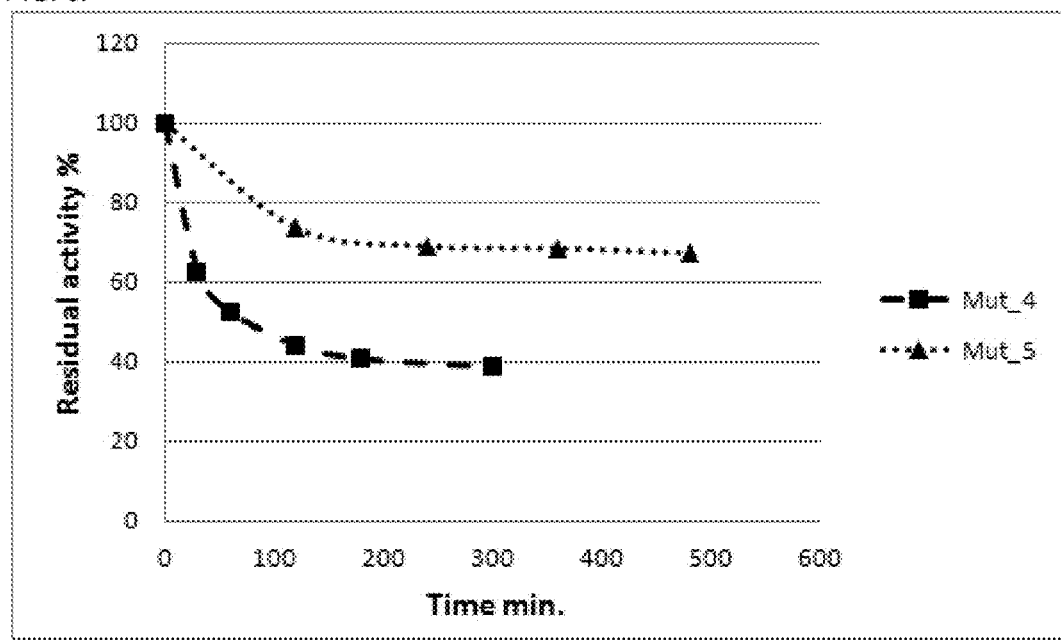

Wild-type phi29 DNA polymerase and mutant enzymes Mut_4 and Mut_5 half-lifes (T$_{1/2}$) of activity were measured in the presence (FIGS. 3D-F) and absence of substrate (FIGS. 3A-C), at either 30° C. (FIGS. 3A, D), 37° C. (FIGS. 3B, E), or 40° C. (FIGS. 3C, F). Wild-type phi29 DNA polymerase half-lives (T$_{1/2}$) of activity without substrate at 30° C. and 37° C. were 18 min and <3 minutes respectively (FIG. 3, Table 1).

TABLE 1

Wild-type and mutant phi29 DNA polymerases half-life (T$_{1/2}$) activity without substrate

|  | T$_{1/2}$ at 30° C. | T$_{1/2}$ at 37° C. | T$_{1/2}$ at 40° C. |
|---|---|---|---|
| Wt | 18 min | <3 min | — |
| Mut_4 | 16 hr | 20 min | 8 min |
| Mut_5 | >16 hr | 16 hr | 15 min |

Mut_4 mutant with M8R, V51A, M97T, G197D, E221K mutations;
Mut_5 mutant with M8R, V51A, M97T, G197D, E221K, Q497P, K512E, F526L mutations Mutant enzymes Mut_4 and Mut_5 were substantially more thermostable and lost half of their activity after 16 hours at 30° C., and after 20 minutes at 37° C. Mut_4 and Mut_5 half-lives (T$_{1/2}$) of activity were also measured at 40° C. and were 8 min and 15 min, respectively. Wild type enzyme at 40° C. lost activity immediately.

All variants of phi29 enzyme were stabilized in the complex with substrate. Wild-type phi29 DNA polymerase half-lives (T$_{1/2}$) of activity with substrate at 30° C. and 37° C. were 100 min and 15 minutes, respectively (FIG. 3, Table 2).

TABLE 2

Wild-type and mutant phi29 DNA polymerases half-life (T$_{1/2}$) activity with substrate

|  | T$_{1/2}$ at 30° C. | T$_{1/2}$ at 37° C. | T$_{1/2}$ at 40° C. |
|---|---|---|---|
| Wt | 100 min | 15 min | — |
| Mut_4 | >16 hr | 16 hr | 1 hr |
| Mut_5 | >16 hr | >16 hr | 16 hr |

Mut_4 mutant with M8R, V51A, M97T, G197D, E221K mutations;
Mut_5 mutant with M8R, V51A, M97T, G197D, E221K, Q497P, K512E, F526L mutations Mutant enzymes Mut_4 and Mut_5 were even more thermostable having half-lives ($T_{1/2}$) of activity with substrate 16 h and more at 30-37° C., and 1 h or 16 h at 40° C. Wild type enzyme, even in a complex with substrate, lost its activity at 40° C. immediately.

Mut_4 mutant variant of phi29 DNA polymerase was substantially more stable compared to wild-type enzyme (FIG. 3, Tables 1 and 2). It was thus concluded that M8R, V51A, M97T, G197D, and E221K amino acids changes are directly involved and responsible for increased enzyme thermostability with and without substrate.

Mut_5 variant of phi 29 DNA polymerase was even more thermostable compared to Mut_4 phi 29 DNA polymerase (FIG. 3, Tables 1 and 2). It was thus concluded that additional Q497P, K512E, and F526L mutations are also important in protein thermostabilization with and without substrate.

Measurement of Half Life ($T_{1/2}$) of Phi29 DNA Polymerase Mutants Containing Single Mutations Nine mutant variants containing single amino acid substitution (M8R, V51A, M97T, G197D, E221K, Q497P, K512E, E515A, F526L) were constructed. Six histidine residues (6×His) (SEQ ID NO: 5) containing tags were fused to the C terminus of wild-type and mutants of phi29 DNA polymerase. His tagged polymerases were purified to more than 95% protein homogeneity using immobilized metal ion affinity chromatography. The thermostability of wild-type, and mutants without and with substrate, was measured at 30° C. and 40° C.

In this example, the half life ($T_{1/2}$) of different phi29 DNA polymerases without substrate was determined using the following protocol.

1. Prepare the following reaction mixture:

|  | For 1 assay | For 10 assays |
|---|---|---|
| 10x Tango buffer | 4 μl | 40 μl |
| H$_2$O | 35 μl | 350 μl |
| phi29 DNA polymerase (100 ng/μl) | 1 μl | 10 μl |
| Total | 40 μl | 400 μl |

(10x Tango buffer: 330 mM Tris-acetate, pH 7.9, 100 mM Mg-acetate, 660 mM K-acetate 1 mg/ml BSA).

2. Incubate samples at 30° C. for 0-150 min (control samples which are incubated for 0 hours refers to 100% of activity).
3. After incubation, transfer samples to an ice bath and add 10 μl solution A.

| Solution A | For 1 assay | For 10 assays |
|---|---|---|
| 10 x Tango buffer | 1 μl | 10 μl |
| Exo-Resistant random primer (500 μM) | 2.5 μl | 25 μl |
| dNTP mix (10 mM) | 5 μl | 50 μl |
| dCTP-$^3$H (37 μM) | 0.25 μl | 2.5 μl |
| Bacteriophage M13 single stranded plasmid DNA (0.805 mg/ml) | 1.25 μl | 12.5 μl |
| Total | 10 μl | 100 μl |

4. Incubate samples at 30° C. for 10 min
5. Stop reaction by adding 5 μl EDTA (0.5 M)
6. Transfer 40 μl of reaction mixture on the DE-81 filter paper (0.5×1.5 cm).
7. Dry papers
8. Wash papers three times with 7.5% Na$_2$HPO$_4$×10 H$_2$O.
9. Wash once with distilled water
10. Dry papers
11. Transfer papers into vials with scintillator and measure cpm. Residual activity is calculated using the following formula:

Residual activity (%)=[cpm (sample)–cpm (blank)]* 100%/[cpm (control sample)–cpm (blank)].

The half life ($T_{1/2}$) of different phi29 DNA polymerases with substrate was determined using the following protocol:

1. Prepare the following reaction mixture:

|  | For 1 assay | For 10 assays |
|---|---|---|
| 10 x Tango buffer | 4.45 μl | 44.5 μl |
| Bacteriophage M13 single stranded plasmid DNA (0.805 mg/ml) | 1.25 μl | 12.5 μl |
| Exo-Resistant random primer (500 μM) | 2.5 μl | 25 μl |
| H$_2$O | 35 μl | 350 μl |
| phi29 DNA polymerase (100 ng/μl) | 1 μl | 10 μl |
| Total | 44.2 μl | 442 μl |

(10x Tango buffer: 330 mM Tris-acetate, pH 7.9, 100 mM Mg-acetate, 660 mM K-acetate 1 mg/ml BSA).

2. Incubate samples at 40° C. for 0-900 min (control samples which are incubated for 0 hours refers to 100% activity).
3. After incubation transfer samples to ice bath and add 5.8 μl solution B.

| Solution B | For 1 assay | For 10 assays |
|---|---|---|
| 10 x Tango buffer | 0.55 μl | 5.5 μl |
| dNTP mix (10 mM) | 5 μl | 50 μl |
| dCTP-$^3$H (37 μM) | 0.25 μl | 2.5 μl |
| Total | 5.8 μl | 58 μl |

4. Incubate samples at 30° C. for 10 min.
5. Stop reaction by adding 5 μl of EDTA (0.5 M).
6. Transfer 40 μl reaction mixture on the DE-81 filter paper (1.5×1.5 cm).
7. Dry papers
8. Wash papers three times with 7.5% Na$_2$HPO$_4$×10 H$_2$O.
9. Wash once with distilled water
10. Dry papers
11. Transfer papers into vials with scintillator and measure cpm. Residual activity is calculated using the following formula:

Residual activity (%)=[cpm (sample)–cpm (blank)] *100%/[cpm (control sample)–cpm (blank)].

Figure 4A:
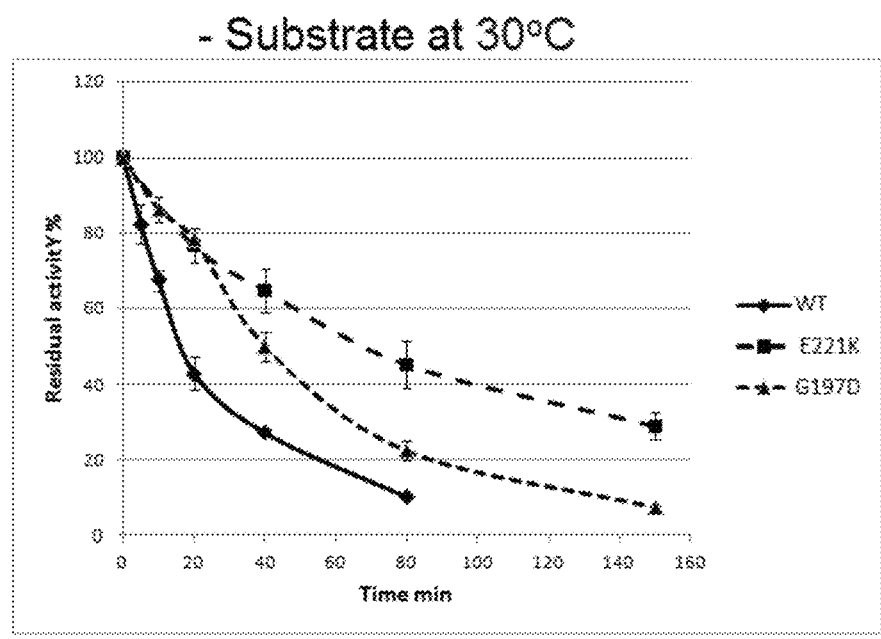
FIGS. 4A-B compare $T_{1/2}$ activities between wild-type phi29 DNA polymerase and mutant variants containing single mutations.

Wild-type phi29 DNA polymerase and mutant enzymes (containing single mutations) half-lives ($T_{1/2}$) of activity were measured in the presence (FIG. 4B) and absence (FIG. 4A) of substrate. Wild-type phi29 DNA polymerase half-lives ($T_{1/2}$) of activity without substrate at 30° C. were 18 min (FIG. 4A, Table 3). Eight mutant enzymes containing single mutations (M8R, V51A, M97T, G197D, E221K, Q497P, E515A, F526L) were more thermostable and lose half their activity at 30° C. after 26, 26, 38, 40, 65, 58, 52, 48 min respectively (FIG. 4A, Table 3).

TABLE 3

Wild-type and phi29 DNA polymerase mutants half-life ($T_{1/2}$) activity with and without substrate

|  | $T_{1/2}$ (min) without substrate, measured at 30° C. (+/−1 SD) | $T_{1/2}$ (min) with substrate, measured at 40° C. (+/−1 SD) |
|---|---|---|
| Wild-type | 18 (2.8) | 37 (2.9) |
| M8R | 26 (2.2) | 195 (3) |
| V51A | 26 (4.1) | 90 (5.5) |
| M97T | 38 (4.3) | 22 (5.7) |
| G197D | 40 (2.7) | 400 (2.8) |
| E221K | 65 (5.1) | 58 (1.9) |
| Q497P | 58 (3.9) | 145 (3.3) |
| K512E | 18 (2.5) | 37 (1.2) |
| E515A | 52 (2.8) | 220 (2.7) |
| F526L | 48 (2.1) | 120 (5.1) |

Figure 4B:
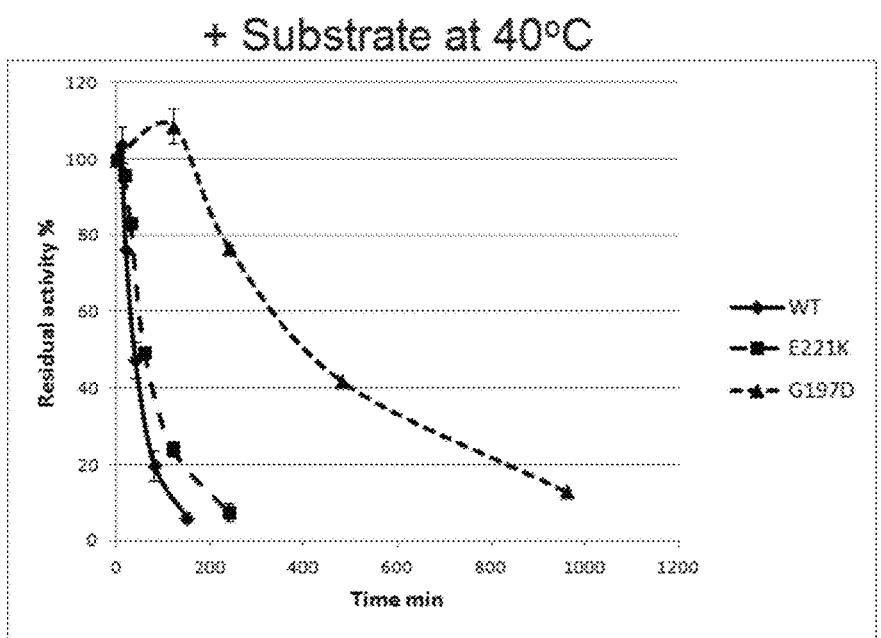

All variants of phi29 enzyme are stabilized in the complex with substrate, therefore half-lives ($T_{1/2}$) of activity could be measured at 40° C. Wild-type phi29 DNA polymerase half-lives ($T_{1/2}$) of activity with substrate at 40° C. were 37 min (FIG. 4B, Table 3). Seven mutant enzymes containing single mutations M8R, V51A, G197D, E221K, Q497P, E515A, F526L were more thermostable having half-lives ($T_{1/2}$) of activity with substrate 195, 90, 400, 58, 145, 220, 120 min respectively (FIG. 4B, Table 3).

EXAMPLE 3

Measurement of MDA Reaction Efficiency at Elevated Temperatures

Multiple displacement amplification (MDA) reaction efficiency was measured at different temperatures. Generation of more MDA product indicates more efficient amplification.

In this example MDA reaction efficiency of different phi29 DNA polymerases was evaluated using the following protocol:

1. Prepare the following MDA reaction mixture:

|  | For 1 assay | For 10 assays |
|---|---|---|
| 10x phi29 buffer | 10 µl | 100 µl |
| 10 mM dNTP Mix | 10 µl | 100 µl |
| Exo-Resistant random primer (500 µM) | 5 µl | 50 µl |
| pUC19 plasmid DNA (10 ng/µl) | 1 µl | 10 µl |
| phi29 DNA polymerase (100 ng/µl) | 1 µl | 10 µl |
| H$_2$O | to 100 µl | To 1000 µl |
| Total | 100 µl | 1000 |

(10x phi29 buffer: 330 mM Tris-acetate, pH 7.9, 100 mM Mg-acetate, 660 mM K-acetate, 1%(v/v) Tween 20, 10 mM DTT)

2. Incubate samples at temperatures of 30° C., 37° C., 42° C., 45° C. for 0.5, 1 and 2 hours then stop the reaction by incubating 15 min at 75° C. Subsequently MDA products are linearized by adding 2 µl restriction endonuclease FD AlwNI (Thermo Fisher Scientific) and incubating for 3 hours at 37° C. and for 10 min at 70° C.

3. To evaluate amplification folds of pUC19 plasmid, MDA products were analyzed by qPCR. The qPCR reaction mixture was prepared as follows:

|  | For 1 assay | For 10 assays |
|---|---|---|
| Maxima SYBR Green qPCR Master Mix (2X) | 12.5 µl | 125 µl |
| Direct primer 5'-GTTGGGAAGGGCGATCG-3' (SEQ ID NO: 6) | 0.75 µl | 7.5 µl |
| Reverse primer 5'-ACTTTATGCTTCCGGCTCGTA-3' (SEQ ID NO: 7) | 0.75 µl | 7.5 µl |
| H$_2$O | 6 µl | 60 µl |
| MDA product diluted with TE buffer | 5 µl | — |
| Total | 25 µl | 200 µl |

Figure 5A:
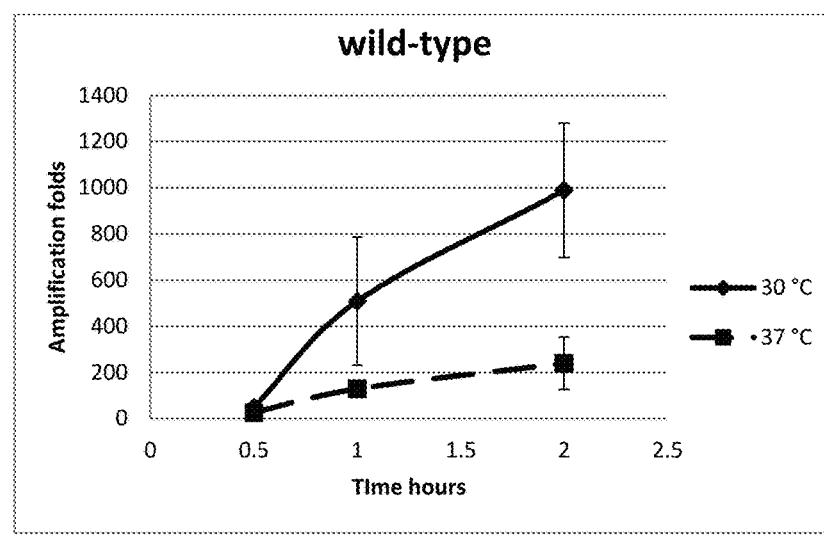
FIGS. 5A-C compares efficiency of multiple displacement amplification (MDA) reaction between wild-type and mutant variants of phi29 DNA polymerase.
Figure 5B:
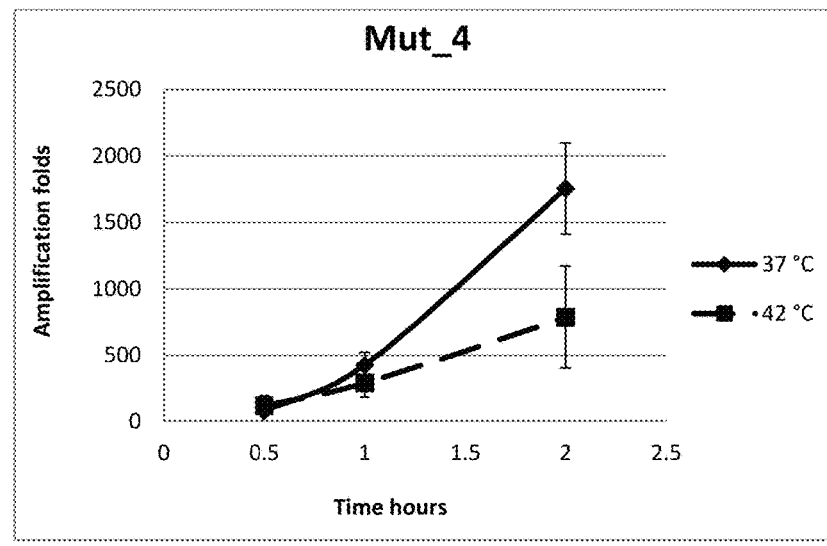
Figure 5C:
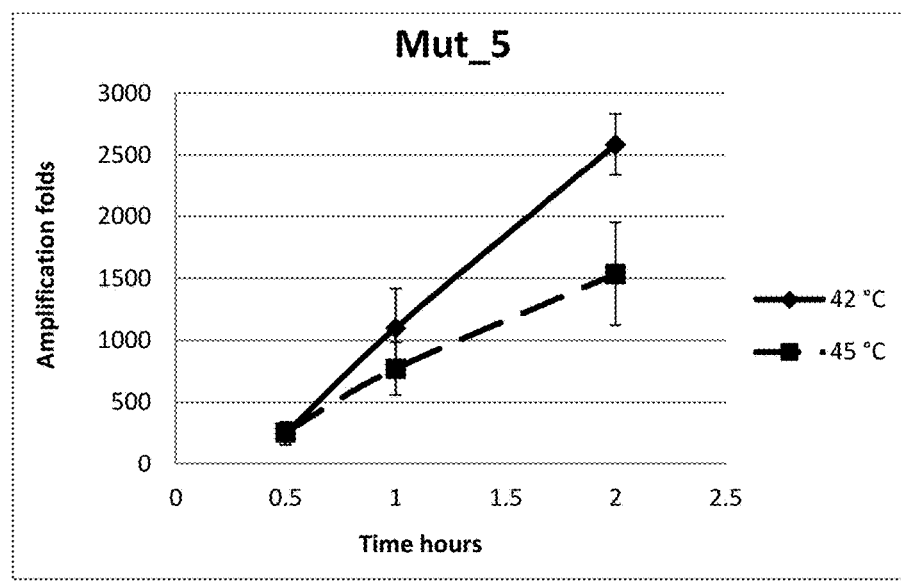

Amplification folds of pUC19 plasmid were calculated using the following formula:
Amplification folds = pUC19 copy number after MDA/pUC19 copy number before MDA MDA reaction at different temperatures was performed using wild-type phi29 DNA polymerase (FIG. 5A) and mutant enzymes Mut_4 (FIG. 5B) and Mut_5 (FIG. 5C). Amplification folds of pUC19 plasmid used as a substrate in MDA reaction were evaluated by qPCR after 0.5, 1 and 2 hours of MDA reaction performed at different temperatures. The results indicated that MDA reaction driven by wild-type phi29 DNA polymerase was more efficient at 30° C. compared to 37° C. (FIG. 5A, Table 4). Mutant enzymes Mut_4 and Mut_5 were able to perform MDA reaction at 37° C., 42° C., and 45° C. (FIG. 5B,C, Table 4), Accumulation of MDA product was about two fold higher using Mut_4 at 37° C. and Mut_5 at 42° C. compared to wild-type enzyme at 30° C. (optimal temperature) (FIG. 5, Table 4). This example showed that mutant phi29 DNA polymerases having more stable protein structure were more stable in the reaction mixture, could work at increased temperatures (37° C.-45° C.), and could generate more amplification product compared to wild-type enzyme.

TABLE 4

Comparison of MDA efficiency between wild-type and mutant variants of phi29 DNA polymerase. Amplification folds of pUC19 plasmid were determined by QPCR.

| Prototype of polymerase (reaction temperature) | MDA reaction duration (hrs) | | |
|---|---|---|---|
|  | 0.5 | 1 | 2 |
| WT (30° C.) | 49 (12) | 509 (277) | 988 (290) |
| WT (37° C.) | 25 (19) | 131 (10) | 241 (113) |
| Mut_4 (37° C.) | 77 (30) | 425 (98) | 1754 (343) |
| Mut_4 (42° C.) | 117 (74) | 288 (108) | 786 (386) |
| Mut_5 (42° C.) | 248 (91) | 1099 (317) | 2585 (249) |
| Mut_5 (45° C.) | 257 (79) | 772 (213) | 1537 (416) |

EXAMPLE 4

Unbiased Whole Genome Amplification

Whole genome amplification (WGA) bias was evaluated by sequencing WGA products obtained using wild-type phi29 DNA polymerase and mutant enzymes Mut_4 and Mut_5. The following scheme was performed:

1. About 20 ng of *E. coli*/JM109 strain gDNA was amplified using wild-type and mutant enzymes Mut_4 and Mut_5. WGA reactions were performed at 30° C., 37° C. and 42° C. for 8 hr, 4 hr, and 3 hr using wild type, Mut_4 and Mut_5 mutant enzymes respectively. Typically as a result of WGA reaction 35 μg-55 μg of DNA were synthesized.
2. DNA synthesized in WGA reaction was sonicated to obtain fragments of an optimal length (300 bp-400 bp). Shared DNA fragments ends were repaired and Illumina sequencing adaptors were ligated using ClaSeek Library Preparation Kit (Thermo Scientific) protocol A. Before bridge amplification and subsequent sequencing reaction DNA fragments were purified using AgenCourt magnetic beads and size selection protocol.
3. Generated NGS libraries were quantified using Kapa Biosystem Library Quantification Kit and sequenced using Illumina MiSeq sequencing platform. Sequencing kit v2 2×150 bp (paired-end) and resequencing protocol was used. Sequences were aligned against *E. coli* K12 strain genomic DNA. A total of 13.8M reads were generated with 94.5 percent of bases called with Q30 and above.

As a "gold standard" for unbiased amplification, reference *E. coli* genome that was not amplified was sequenced (PCR-free NGS library). Sequenced genome coverage data of unamplified *E. coli* genome ("gold standard") and WGA amplified genomes were compared. The coverage evenness graph shown in FIG. 6 demonstrated what coverage average (normalized to 1, X axis) is characteristic for a particular part of genome (Y axis), where coverage evenness (E) shows which part of affected bases is similar to coverage average (1.0). In this example, ~80% of targeted regions of PCR-free gDNA were covered with >0.8 of average coverage and ~20% of reads had >1.2 of average coverage. Coverage evenness number was calculated as described by Mokry et al. 2010. The closer the value is to 1 the better coverage evenness. Sequencing coverage evenness value for WGA amplified DNA library generated using wild type phi29 DNA polymerase was 0.39; E values for Mut_4 and Mut_5 amplified libraries were 0.70 and 0.76, respectively (*E-coli*-gDNA E=0.91 (non amplified *E. coli* gDNA), WI E=0.39 (0.04) (WGA product that was amplified at standard conditions using wild-type phi29 DNA polymerase), Mut_5 E=0.76(0.01) (WGA product that was amplified at 42° C. using mutant polymerase), Mut_4 E=0.70(0.02) (WGA product that was amplified at 37° C. using mutant polymerase).

CG percentage in 100 bp fragments of reads' sequences was calculated for all four sequencing runs (FIG. 7). FIG. 7 depicts the percent of fragments of 100 bp length and CG content in reads. The WGA library that was prepared using wild type enzyme contains more fragments with lower CG content and less percent of fragments with higher CG content. NGS library amplified with wild type phi29 DNA polymerase had a light shift of CG percentage peak to lower CG content. CG percentage peak shift of NGS library amplified by Mut_4 enzyme was smaller compared to wt phi29 polymerase. CG percentage peak of NGS library amplified by Mut_5 enzyme was almost identical to unamplified *E. coli* gDNA data (FIG. 7). It is very likely that wild type enzyme which performed WGA reaction at 30° C. tends to amplify genome regions with lower CG content. The CG amplification bias could be significantly decreased performing WGA with Mut_4 and Mut_5 polymerases at 37° C. and 42° C. respectively. Reduced amplification bias should also result in decrease of allele dropout (ADO) effect.

EXAMPLE 5

DNA Binding Assay of Phi29 Polymerase Mutants

Electrophoretic mobility shift assay (EMSA) was performed using as substrate labeled hybrid 15-mer/21-mer DNA molecule to determine whether novel mutations of phi29 DNA polymerase enhanced enzyme binding to DNA. Oligonucleotide 15-mer (5-GATCACAGTGAGTAC-3') (SEQ ID NO: 8) was 5'-labeled with [γ-$^{32}$P] ATP using T4 polynucleotide kinase and hybridized with 21-mer (5'-TCTATTGTACTCACTGTGATC-3') (SEQ ID NO: 9) in the presence of 0.2 M NaCl and 60 mM Tris-HCl, pH 7.5 (De Vega, M. et al. 2010). The resulting 5'-labeled 15-mer/21-mer hybrid molecule was used as DNA primer/template to analyze the interaction with either wild-type phi29 or mutant enzymes containing single or multiple mutations. The incubation mixture contained, in a final volume of 20 μl, 33 mM Tris-acetate pH 7.9, 66 mM potassium acetate, 10% glycerol, 0.1 mg/ml BSA, 2 pM of the labeled 15-mer/21-mer DNA/DNA substrate, and increasing amounts of the corresponding enzyme (0, 10, 20, 40, 80, 160, 300, 600 pM). After incubation for five min at 30° C., samples were subjected to electrophoresis in 10% (w/v) polyacrylamide gels (29:1, acrylamide:bisacrylamide) containing 40 mM Tris-acetate pH 8.4, 1 mM EDTA (1×TAE buffer). Electrophoresis was performed in the same 1×TAE buffer at room temperature for two hours at about 8-9 V/cm. The EMSA gels were analyzed by Typhoon Trio and OptiQuant™ Image Analysis Software. Enzyme-oligonucleotide complex Kd values were calculated by GraphPad Prism version 4.03 software using the equation: $[DNA\text{-}E]=([DNA_o]+[E_o]+K_d-(([DNA_o]+[E_o]+K_d)^2-4[DNA_o][E_o]^{0.5})/2$; where [DNA-E]—is enzyme oligonucleotide complex concentration, [$DNA_o$]—total oligonucleotide concentration (2 pM), [$E_o$]—total enzyme concentration.

FIG. 8 shows a representative EMSA of wt, Mu_4 and Mut_5 enzyme binding to DNA. The 5'-labeled hybrid molecule 15mer/21mer (dsDNA) was incubated with phi29 DNA polymerase or with the mutant DNA polymerase. After gel electrophoresis, the mobility of free dsDNA and the polymerase-DNA complex was detected by autoradiography. FIG. 8 is representative of several experiments (experiments with mutants containing single mutations not shown). All the numerical values of dissociation constant determined by EMSA assay are summarized in Table 5.

TABLE 5

Dissociation constants (Kd) of phi29 DNA polymerase mutants

| | Kd (SD) | | Kd (SD) |
|---|---|---|---|
| WT | 76 (5.7) | Q497P | 73 (50.2) |
| M8R | 43 (2.1) | K512E | 54 (27.6) |
| V51A | 52 (10.8) | E515A | 97 (56.5) |
| M97T | 37 (2.5) | F526L | 53 (24.2) |
| G197D | 51 (25.7) | Mut_4 | 67 (10.6) |
| E221K | 67 (18.4) | Mut_5 | 23 (7.4) |

Mutant enzymes exhibited improved DNA binding (lower Kd), requiring about twofold or threefold lower enzyme concentration compared to the wild-type polymerase to generate similar amount of DNA protein complex. Dissociation constant (Kd) values of some mutants containing single mutations (M8R, V51A, M97T) as well as Mut_5 polymerase were lower than wild-type phi29 DNA polymerase (Table 5). De Vega et al. 2010 showed that phi29

DNA polymerase with additional DNA binding domain has increased affinity to substrate, and subsequently other enzyme features as processivity and amplification yield were also improved. As the disclosed phi29 DNA polymerase mutants also possess increased affinity to substrate, it was reasonable to expect that such mutants will show improvements in other important characteristics of this enzyme.

Each of the following references is expressly incorporated by reference herein in its entirety.

1. Akeson et al. (2010) Processive Replication of single DNA molecules in a nanopore catalyzed by phi29 DNA polymerase. *J. Am. Chem. Soc*. Vol. 132 No. 50 pp. 17961-17972
2. Alsmadi et al. (2009) Specific and complete human genome amplification with improved yield achieved by phi29 DNA polymerase and a novel primer at elevated temperature. BMC Research Notes. 2:48.
3. Blanco et al. (1989) Highly efficient DNA synthesis by phage phi29 DNA polymerase. Symmetrical mode of DNA replication. *J Biol Chem*. Vol. 264, No. 15, pp. 8935-8940
4. Bernad et al. (1987) Structural and functional relationships between prokaryotic and eukaryotic DNA polymerases. *EMBO J*. Vol. 6, No. 13, pp. 4219-4225.
5. Berman et al. (2007) Structures of phi29 DNA polymerase complexed with substrate: the mechanism of translocation in B-family polymerase. *EMBO J*. Vol. 26, No. 14, pp. 3494-3505, ISSN 0261-4189 (Print).
6. Dufour et al. (2000) An aspartic acid residue in TPR-1, a specific region of protein-priming DNA polymerase, is required for the functional interaction with primer terminal protein. *J Mol Biol*. Vol 304, No. 3, pp. 289-300
7. Esteban et al. (1993) Fidelity of phi29 DNA polymerase. Comparison between protein-primed initiation and DNA polymerization. J Biol Chem. Vol. 268, No. 4, pp. 2719-2726.
8. Esteban et al. (1994) 3'-5' exonuclease active site of phi29 DNA polymerase. Evidence favoring a metal ion-assisted reaction mechanism. *J Biol Chem*. Vol. 269, No. 50, pp. 31946-31954
9. Ghadessy et al. (2001) Directed evolution of polymerase function by compartmentalized self-replication Proc. Natl Acad. Sci. USA, 98, 4552-4557.
10. Hutchison et al. (2005) Cell-free cloning using phi29 DNA polymerase. PNAS. Vol. 102, No. 48, pp. 17332-17336.
11. Johne et al. (2009) Rolling-circle amplification of viral DNA genomes using phi29 polymerase. Trends in Microbiology. Vol 17, No 5, pp. 205-211.
12. Kamtekar et al. (2004) Insights into strand displacement and processivity from the crystal structure of the protein-primed DNA polymerase of bacteriophage phi29. Mol Cell. Vol. 16, No. 4, pp. 609-618
13. Lagunavicius et al. (2010) Direct detection of RNA in vitro and in situ by target-primed RCA: The impact of *E. coli* RNase III on the detection efficiency of RNA sequences distanced far from the 3'-end. RNA. Vol. (16) No. 8 pp. 1508-1515
14. Lasken et al. (2003) Unbiased whole-genome amplification directly from clinical samples. Genome Research. Vol. 13 pp. 954-964
15. Lizardi et al. (1998) Mutation detection and single-molecule counting using isothermal rolling-circle amplification. Nat Genet, 19, 225-232
16. De Vega et al. (2010) Improvement of phi29 DNA polymerase amplification by fusion of DNA binding motifs. *Proc. Natl. Acad. Sci. U.S.A*. Vol. 107, No. 38, pp. 16506-16511.
17. Mokry et al. (2010) Accurate SNP and mutation detection by targeted custom microarray-based genomic enrichment of short-fragment sequencing libraries. *Nucleic Acids Res*. Vol. 38, No. 10, pp. e116.
18. Rodriguez et al. (2005) A specific subdomain in phi29 DNA polymerase confers both processivity and strand-displacement capacity. *Proc Natl Acad Sci USA*. Vol. 102, No. 18, pp. 6407-6412
19. Salas and de Vega (2006) Bacteriophage protein-primed DNA replication. In Recent advances in DNA virus replication. Hefferon, K. L., pp. 259-288, Research Signpost, ISBN 81-3080042-X, Kerala (India)
20. Simmel et al. (2005) Periodic DNA Nanotemplates Synthesized by Rolling Circle Amplification. *Nano Letters*. 4, -pp. 719-722
21. Weissman et al. (2008) A procedure for highly specific, sensitive, and unbiased whole-genome amplification. PNAS. Vol. 105 No. 40 pp. 15499-15504

The embodiments described in the specification are only specific embodiments of the inventors who are skilled in the art and are not limiting. Therefore, various changes, modifications, or alterations to those embodiments may be made without departing from the spirit of the invention or the scope of the following claims.

This application contains a Sequence Listing which has been submitted electronically in ASCII format and is hereby incorporated by reference in its entirety. The ASCII copy, created on Dec. 19, 2013, is named 077792.43_SL.txt and is 156,299 bytes in size.

What is claimed is:

1. A method for amplifying a deoxyribonucleic acid (DNA), the method comprising contacting a DNA to be amplified with a mutant bacteriophage phi29 DNA polymerase comprising from one to thirteen mutations relative to wild-type phi29 DNA polymerase (SEQ ID NO: 10), wherein the at least one mutation is selected from group consisting of M8R, V51A, M97T, L123S, K209E, E221K, Q497P, and E515A, and
    incubating the mutant bacteriophage phi29 DNA polymerase and the DNA to be amplified at a temperature greater than 30° C. under conditions to result in an amplified DNA.

2. The method of claim 1 where the bacteriophage phi29 DNA polymerase comprises the mutations M8R, V51A, M97T, G197D, and E221K.

3. The method of claim 1 where the bacteriophage phi29 DNA polymerase comprises the mutations M8R, V51A, M97T, G197D, E221K Q497P, K512E, and F526L.

4. The method of claim 1 where the mutant bacteriophage phi29 DNA polymerase generates a higher amount of DNA amplification product compared to wild-type phi29 DNA polymerase.

5. The method of claim 1 where the mutant bacteriophage phi29 DNA polymerase has a higher degree of DNA polymerase fidelity compared to wild-type phi29 DNA polymerase.

6. The method of claim 1 where the mutant bacteriophage phi29 DNA polymerase has a longer half-life compared to wild-type phi29 DNA polymerase.

7. The method of claim 1 where the bacteriophage phi29 DNA polymerase has increased catalysis compared to wild-type phi29 DNA polymerase.

8. The method of claim 1, wherein the sequence of the bacteriophage phi29 DNA polymerase is selected from the group consisting of SEQ ID NOS 11-13, 16-39 and 40.

9. The method of claim 1, wherein the sequence of the bacteriophage phi29 DNA polymerase comprises the mutation M8R.

10. The method of claim 1, wherein the sequence of the bacteriophage phi29 DNA polymerase comprises the mutation V51A.

11. The method of claim 1, wherein the sequence of the bacteriophage phi29 DNA polymerase comprises the mutation M97T.

12. The method of claim 1, wherein the sequence of the bacteriophage phi29 DNA polymerase comprises the mutation L123S.

13. The method of claim 1, wherein the sequence of the bacteriophage phi29 DNA polymerase comprises the mutation K209E.

14. The method of claim 1, wherein the sequence of the bacteriophage phi29 DNA polymerase comprises the mutation E221K.

15. The method of claim 1, wherein the sequence of the bacteriophage phi29 DNA polymerase comprises the mutation Q497P.

16. The method of claim 1, wherein the sequence of the bacteriophage phi29 DNA polymerase comprises the mutation E515A.

17. A method for amplifying a deoxyribonucleic acid (DNA), the method comprising contacting a DNA to be amplified with a mutant bacteriophage phi29 DNA polymerase of SEQ ID NO: 14 or SEQ ID NO: 15, and
    incubating the mutant bacteriophage phi29 DNA polymerase and the DNA to be amplified at a temperature greater than 30° C. under conditions to result in an amplified DNA.

* * * * *